(12) United States Patent
Bulsara et al.

(10) Patent No.: US 11,357,712 B2
(45) Date of Patent: *Jun. 14, 2022

(54) METHOD OF USE AND COMPOSITIONS

(71) Applicant: LG HOUSEHOLD & HEALTH CARE LTD., Seoul (KR)

(72) Inventors: Pallav Arvind Bulsara, Warren, NJ (US); Martyn J. Clarke, Zebulon, NC (US); Zheng Guo, Aarhus (DK); Bianca Pérez, Aarhus (DK); Anthony V. Rawlings, Cheshire (GB)

(73) Assignee: LG HOUSEHOLD & HEALTH CARE LTD., Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/876,179

(22) Filed: May 18, 2020

(65) Prior Publication Data

US 2021/0030638 A1 Feb. 4, 2021

Related U.S. Application Data

(63) Continuation of application No. 15/770,856, filed as application No. PCT/US2016/058591 on Oct. 25, 2016.

(60) Provisional application No. 62/247,803, filed on Oct. 29, 2015.

(51) Int. Cl.
| | | |
|---|---|---|
| *A61K 8/06* | (2006.01) | |
| *A61K 8/34* | (2006.01) | |
| *A61K 8/37* | (2006.01) | |
| *A61K 8/55* | (2006.01) | |
| *A61K 9/107* | (2006.01) | |
| *A61K 9/00* | (2006.01) | |
| *A61K 47/14* | (2017.01) | |
| *A61K 8/02* | (2006.01) | |
| *A61K 8/36* | (2006.01) | |
| *A61Q 19/00* | (2006.01) | |

(52) U.S. Cl.
CPC ............ *A61K 8/062* (2013.01); *A61K 8/0295* (2013.01); *A61K 8/342* (2013.01); *A61K 8/361* (2013.01); *A61K 8/375* (2013.01); *A61K 8/553* (2013.01); *A61K 9/0014* (2013.01); *A61K 9/107* (2013.01); *A61K 47/14* (2013.01); *A61Q 19/00* (2013.01); *A61Q 19/007* (2013.01)

(58) Field of Classification Search
CPC ........ A61K 8/062; A61K 8/375; A61K 8/553; A61K 8/361; A61K 47/14; A61K 8/0295; A61K 8/342

See application file for complete search history.

(56) References Cited

U.S. PATENT DOCUMENTS

| | | |
|---|---|---|
| 5,849,315 A | 12/1998 | Rerek et al. |
| 6,051,250 A | 4/2000 | Ribier et al. |
| 6,986,903 B2 | 1/2006 | Zulli et al. |
| 2012/0108661 A1 | 5/2012 | Orita et al. |
| 2013/0324499 A1 | 12/2013 | Pennick et al. |
| 2015/0147403 A1 | 5/2015 | Djedour |

FOREIGN PATENT DOCUMENTS

| | | |
|---|---|---|
| EP | 2 670 376 A2 | 12/2013 |
| EP | 2 926 833 A1 | 10/2015 |
| JP | 2000-247987 A | 9/2000 |
| JP | 2011-32266 A | 2/2011 |
| JP | 2011-178748 A | 9/2011 |
| JP | 2013-18751 A | 1/2013 |
| WO | WO 2013/007599 A2 | 1/2013 |

OTHER PUBLICATIONS

Japanese Office Action—Notice of Reasons for Refusal, 16 pages with English translation, dated May 22, 2019.
Korean Office Action—Notification of Reason for Refusal, 14 pages with English translation, dated Jul. 1, 2019.
Bianca P Rez et al.: "Ultralong Fatty Acyl Derivatives as Occlusive Structure Lipids for Cosmetic Applications: Synthesis and Characterization", ACS Sustainable Chemistry & Engineering, vol. 4, No. 12; Sep. 26, 2016 (Sep. 26, 2016), pp. 7137-7146, XP055589871, ISSN: 2168-0485, DOI: 10.1021/acssuschemeng.6b02021.
EP Search Report dated Jun. 3, 2019.
Pennick et al. "The effect of an amphiphilic self-assembled lipid lamellar phaseon the relief of dry skin." Intl J Cosmetrc Sci, 2012, vol. 34, pp. 567-574 abstract, p. 568, col. 2, Table 1, p. 570, Fig 1.

*Primary Examiner* — Shobha Kantamneni
(74) *Attorney, Agent, or Firm* — Vorys, Sater, Seymour & Pease; Mih Suhn Koh

(57) ABSTRACT

The present invention is directed to a method for improving the occlusiveness of a topical pharmaceutical or cosmetic formulation in use in a patient in need thereof, comprising adding to the formulation at least 0.1- to about 10% w/w of one or more of a monofatty acid ester of glycerin and/or one or more of a monofatty acid ester of glycol, or mixtures thereof.

The present invention is also directed to a method for maintaining skin barrier efficiency of the stratum corneum of a patient in need thereof, comprising applying to the skin of said patient a pharmaceutical or cosmetic formulation containing at least 3% w/w of one or more of a monofatty acid ester of glycerin and/or one or more of a monofatty acid ester of glycol, or mixtures thereof.

13 Claims, 2 Drawing Sheets

METHOD OF USE AND COMPOSITIONS

BACKGROUND OF THE INVENTION

The skin serves an important role as a barrier to protect the body from the harsh external environment and from foreign agents but this function can be compromised in diseased or xerotic skin conditions. The stratum corneum (SC), the outermost layer of the skin, provides a barrier between the external environment and the deeper layers of the skin offering protection from penetration of irritant chemicals and microbes while reducing transepidermal water loss (TEWL) from the skin (V. Rawlings, Br J Dermatol, 171 Suppl 3 (2014) 19-28). The structure of SC can be described as a 'brick wall' structure where the bricks refer to the corneocytes and the mortar between the bricks is the lipid-rich matrix. (Rawlings, supra; A. S. Michaels, et al., AIChE J, 21 (1975) 985-996; J. van Smeden, et al., Biochim Biophys Acta, 1841 (2014) 295-313

Face, Hand and Body lotions have an important role to play in maintaining and improving SC barrier function as well as in eliminating the negative symptoms associated with dry skin including dryness, the sensation of itchiness, and the appearance of skin scaliness (A. V. Rawlings et al., Int J Cosmet Sci, 25 (2003) 63-95; A. V. Rawlings, et al., Dermatol Ther, 17 Suppl 1 (2004) 49-56; A. V. Rawlings, et al., J Invest Dermatol, 124 (2005) 1099-1110). Among different factors contributing to dry skin are the use of household detergents and personal cleansers. For instance, detergents have made dermatitis one of the most common occupational diseases in developed countries. These products deplete or disrupt the lipid matrix of the SC, and consequently the skins' ability to act as a barrier (G. Imokawa, et al., Arch Dermatol Res, 281 (1989) 45-51; and A. V. Rawlings, J Soc Cosmet Chem, 45 (1994) 203-220). In general, treatments include the use of moisturizing ingredients to increase skin hydration (M. Loden, Am J Clin Dermatol, 4 (2003) 771-788; and Loden, Clin Dermatol, 30 (2012) 286-296).

Moisturizers may be used to maintain or repair the skin's barrier efficiency under the above conditions. Occlusive technologies such as petrolatum are used to achieve this by reducing transepidermal water loss through the skin. Moisturizers often also contain a humectant such as glycerin which is a highly hygroscopic organic molecule that increases skin hydration by retarding water loss from a topical product, by absorbing water from the environment and preventing its loss through the skin via the transepidermal barrier. This is often measured via a water transmission vapor loss test (WVTR).

In addition to humectants, emollient and occlusive agents are also used in skin care formulations that help to hydrate the skin by providing an occlusive layer on the surface of the skin or modulate the phase behavior of endogenous lipids within the skin which directly reduces TEWL (V. Rawlings, et al., Int J Cosmet Sci, 34 (2012) 511-518; G. Pennick, et al., Int J Cosmet Sci, 32 (2010) 304-312; J. C. Dederen, et al., Int J Cosmet Sci, 34 (2012) 502-510; J. Caussin, et al., Exp Dermatol, 16 (2007) 891-898; J. Caussin, et al., Skin Pharmacol Physiol, 20 (2007) 175-186; J. Caussin, et al., Biochim Biophys Acta, 1778 (2008) 1517-1524; and J. A. Bouwstra, et al., Int J Cosmet Sci, 34 (2012) 560-566). A well-known example of an occlusive technology agent as noted above is Petrolatum (See D. S. Morrison, Petrolatum: A useful classic, Cosmetics & Toiletries, 111 (1996) 59-69). Petrolatum is a mixture of hydrocarbons derived from petroleum and is frequently used in skin care products. (T. A. Stortz, et al., Green Chemistry, 16 (2014) 3064-3070). However, petrolatum has poor sensory attributes that can adversely affect patient and consumer compliance rates. Ceramides, pseudoceramides, phospholipids have been used as barrier lipids but are still relatively expensive (E. Berardesca, et al., Contact Dermatitis, 45 (2001) 280-285; G. Imokawa, et al., J Clin Invest, 94 (1994) 89-96; Y. Takagi, et al., Dermatology, 211 (2005) 128-134; R. S. Summers, et al., J Soc Cosmet Chem, 47 (1996) 27-39; G. Pennick, et al., Int J Cosmet Sci, 34 (2012) 567-574). The use of skin care formulations containing derivatives of longer chain fatty acids linked to ceramides, cholesterol or sphingosines has also been found to be capable of mimicking the behavior of naturally-occurring lipids in the SC (see AV. Rawlings, Int J Cosmet Sci, 25 (2003) 63-95).

A series of patent filings from Kao Corporation, as will be further described below, claim a lamellar alpha gel structure of sphingosines, or sphingosine like compounds, a ceramide, long chain alcohols, water, polymer and/or a co-polymers along with a glycerol mono-fatty acid ester of 12-22 carbon atoms. The emulsion like compositions are stated to provide a film with softness and elasticity, have high moisture retention power and smoothness to the skin. Some of these patent/application also contain anionic and cationic surfactants, etc.

KAO Corporation, JP 4926420 (corresponding to JP 2007-022997), Oda et al., appears to be the earliest of the filings by this company that cover a lamellar alpha gel structure having an emulsified composition of components (A) to (F) with a specific mass ratio of the component to each other. Component (A) appears to be a sphingosine, a pseudo sphingosine or a compound which is an anionic surfactant or a quaternary ammonium salt, a C12-C24 aliphatic acid, a POE phosphate and a long chain N-acyl (C12-C24) glutamate. The (B) component is a ceramide of general formula (5) (described therein). The (C) component is a glycerine mono fatty acid ester. The (D) component is a C10-C24 higher alcohol. The (E) component is water. The (F) component is a polyhydric alcohol.

KAO Corporation patent filing WO 2013/22037, corresponding to US 2014/0194522, Kaizu et al., appears to describe a lamellar alpha gel structure (liquid crystal structure) composition of (A)-(F) components. In this publication, the (A) component is a glyceryl mono-fatty acid ester derived from a linear chain fatty acid having 10 to 24 carbon atoms. The (B) component is a higher alcohol having 10 to 24 carbon atoms. The (C) component is a ceramide. The (D) component is an anionic surfactant. The (E) component is polar oil selected from branched fatty acid esters having an IOB of from 0.2 to 0.85 and having a hydroxyl group or an amino group. The (F) component is water. The mass ratio of the total content of ingredients (A), (B), (C), and (D) in terms of acid to the content of ingredient (E), ((A)+(B)+(C)+(D))/(E), is from 1.2 to 25.

KAO Corporation patent filing WO 2013/180157, corresponding to US 2015/0133550, Orita et al., describe a lamellar alpha gel structure (liquid crystal structure) composition of (A)-(D) components. The (A) component is a sphingosine or a salt thereof, (see formula 1 therein), a pseudo-sphingosine or a salt thereof, and an ionic surfactant. The (B) component is at least one compound selected from the group consisting of a mono glyceryl di-fatty acid ester and a sorbitan di-fatty acid ester. The (C) component is at least one compound selected from the group consisting of a ceramide, an alcohol having 12 to 22 carbon atoms, a mono glyceryl mono-C12 to C22 fatty acid ester, a mono-C12 to C22 alkyl glyceryl ether, and a sorbitan mono-C12 to C22 fatty acid ester. The (D) component is water. The ingredients (A), (B), and (C), have a specific weight ratio or molar ratio to each other as described therein.

KAO Corporation patent filing WO 2014/87955, Ueyama et al., (machine translation), appears to describe an emulsion cosmetic composition with components (A)-(D) with particular ratios of (A), (B) and (C) to each other. The (A) component appears to be 2 or more compounds selected from a sphingosine salt and an ionic surfactant. The (B) component is a linear glycerol di-fatty acid ester, a linear sorbitan di-fatty acid ester. The (C) component is a compound represented by formula (3) as described therein, an alcohol of C12-22 carbon atoms, a glycerol mono-fatty acid ester of C12-22 or the like. In one instance the (C) component of formula (3) is described as a natural ceramide and pseudo ceramide. The (D) component is a powder with a particular diameter size and (E) is water.

WO 2015/052754 describes (via a machine translation), a cosmetic composition of a particular viscosity that is comprised of (A), (B) and (C) wherein (A) comprises a structural unit represented by general formula (1)(a), (2)(b) or formula (3),

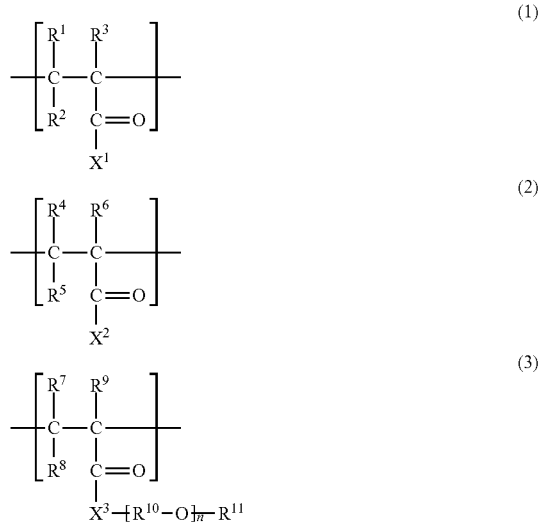

(B) at least one selected from the following (B1)-(B5) oily components including, (B1) 1 or more selected from carbon atoms 14 or more glyceryl mono fatty acid ester and Sorubitanji fatty esters having 14 or more carbon atoms, (B2) a carbon number of 14 or more glycerol monoalkyl ethers, (B3) a higher alcohol having more than 14 carbon atoms, (B4) a higher fatty acid having 14 or more carbon atoms, (B5) a ceramide or ceramide derivative, and (C) water.

KAO Corporation, JP 2014108954, Ueyama et al., (machine translation) appears to describe a lamellar alpha gel structure (liquid crystal structure) with components (A) to (F), with particular ratios to each other and includes a compound, an anionic surfactant, a glycerine mono fatty acid ester of formula (1), a higher alcohol, N-acyl glutamate and a powder to achieve a moisture retaining effect.

The KAO patent filings appear to require a combination of lipid components that provide skin-like similarities as measured by WAXS (Wide Angle X ray Scattering). In general, the filings seem to be focused on keeping the ceramide in the systems in a non-crystalline state (i.e. a physically stable system).

WAXS provides information about the lateral packing character (i.e. hexagonal or orthorhombic) of the ∝ gel structure referred to in the patent. It is generally defined as a hexagonal crystal structure type, in which an oleophilic group is arranged perpendicular to the hydrophilic group layer, with one characteristic diffraction peak at a Bragg angle of around 21 to 23°. No specific data for WAXS is presented in the KAO patent filings, but statements are made to the fact that an ∝ gel structure is formed. Neither is specific data on reductions in moisture loss presented, although sensory scores are given.

Hoyu Company, Ltd. JP 2014201575, Matsubayashi Jun, (machine translation) appears to describe a preparation which includes oil-in-water type liquid crystal structure that is not tacky and which comprises a (A), (B) and (C) wherein (A) is at normal temperatures a solid higher alcohol; (B) is a glycerine fatty acid ester and (C) is an ester oil that is not (B) (and it is from the ester of a fatty acid and the higher alcohol). It appears that the (C) component may be myristyl myristate, cetyl palmitate, or octyl dodecyl myristate. The (A) component can be amongst others: myristyl alcohol, cetyl alcohol, stearyl alcohol, behenyl alcohol, arachidyl alcohol, cetostearyl alcohol, or lanolin alcohol. The (B) component is a glycerin fatty acid ester or a polyglycerine fatty acid having a C12 to 18 aliphatic acid, suitably a self-emulsifying type, such as those listed therein. The application also appears to require a water soluble polymer.

Thus, it is important to find consumer acceptable, sustainable, green, and commercially viable moisturizer alternatives for indications such as xerosis, that better mimic the skins' own lipid organization and physical properties. The present invention is believed to provide such an alternative.

SUMMARY OF THE INVENTION

Figure 1:
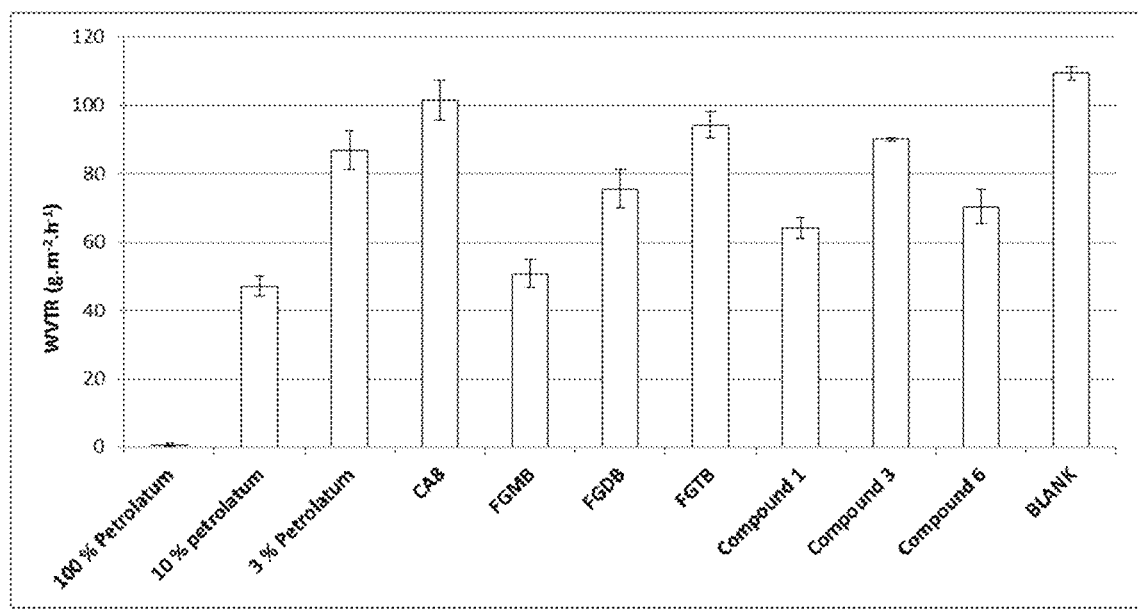
FIG. 1 shows WVTR results for fractionated and synthesized behenoyl lipids.

One aspect of the invention is a method for improving the occlusiveness of a pharmaceutical or cosmetic formulation in use in a patient in need thereof, comprising adding to the formulation at least 0.1 to about 10% w/w of one or more of a monofatty acid ester of glycerin and/or one or more of a monofatty acid ester of glycol, or mixtures thereof. In one embodiment, the amount of the one or more of a monofatty acid ester of glycerin and/or one or more of a monofatty acid ester of glycol, or mixtures thereof in the formulation is >3% w/w. In another embodiment, the amount of is >5% w/w. In an embodiment, the ethyleneglycol monoglyceride is a mixture of ethylene glycol monoglyceride and behenoyl monoglyceride. In an embodiment the behenoyl monoglyceride is a mixture of monobehenate and glycerides of shorter fatty acyl chain lengths. In an embodiment at least 85% of the mixture is the monobehenate ester. In another embodiment, the composition does not comprise an anionic surfactant. In another embodiment, the composition is free from or substantially free from all conventional surfactants.

In an embodiment, the pharmaceutical or cosmetic formulation further comprises an oil such as caprylic/capric triglyceride, a phospholipid such as phosphatidylcholine present as a mixture of C16 and C18 saturated acyl chains, and water. In an embodiment the pharmaceutical or cosmetic formulation further comprises pentylene glycol, glycerin and gelling agents, and optionally other dermatologically acceptable excipients.

Another aspect of the invention is a method for improving skin surface moisturization in the stratum corneum of a patient in need thereof, comprising applying to the stratum corneum of said patient a pharmaceutical or cosmetic formulation containing at least 0.1 to about 10% w/w of one or more of a monofatty acid ester of glycerin and/or one or more of a monofatty acid ester of glycol, or mixtures thereof. In one embodiment, the amount of the one or more of a monofatty acid ester of glycerin and/or one or more of a monofatty acid ester of glycol, or mixtures thereof in the formulation is >3% w/w. In another embodiment, the amount of is >5% w/w. In an embodiment, the ethyleneglycol monoglyceride is a mixture of ethylene glycol monoglyceride and behenoyl monoglyceride. In an embodiment the behenoyl monoglyceride is a mixture of monobehenate and glycerides of shorter fatty acyl chain lengths. In an embodiment at least 60% of the mixture is the monobehenate ester. In another embodiment at least 85% of the mixture is the monobehenate ester. In another embodiment the behenoyl monoglyceride is a mixture of monobehenate and glycerides of longer fatty acyl chain lengths. In an embodiment, the glycerides of longer or shorter fatty acyl chain lengths are monoglycerides.

Glycerol has 3 positions with 3-hydroxyl groups. The mono-substitution of the hydroxyl moiety can occur at any position. One aspect of this invention is a monofatty acid ester of glycerin substituted in the 1-position of the glycerin molecule. Another aspect of the invention is a monofatty acid ester of glycerin substituted in the 2-position of the glycerin molecule. As used herein the one or more of a monofatty acid ester of glycerin could be substituted in either position of the glycerol moiety and can encompass both isomers of the compound as a mixture.

In an embodiment the formulation may further comprise an oil which is caprylic/capric triglyceride, a phospholipid which is phosphatidylcholine (as a mixture of C16 and C18 saturated acyl chains), and water. In an embodiment, the formulation may further comprise pentylene glycol, glycerin and gelling agents, an optionally other dermatologically acceptable excipients.

Another aspect of the invention is a method for improving surface textural properties of the stratum corneum of a patient in need thereof, comprising applying to the stratum corneum of said patient a pharmaceutical or cosmetic formulation containing at least 0.1 to about 10% w/w of one or more of a monofatty acid ester of glycerin and/or one or more of a monofatty acid ester of glycol, or mixtures thereof. In one embodiment, the amount of the one or more of a monofatty acid ester of glycerin and/or one or more of a monofatty acid ester of glycol, or mixtures thereof in the formulation is >3% w/w. In another embodiment, the amount of is >5% w/w. In an embodiment, the ethyleneglycol monoglyceride is a mixture of ethylene glycol monoglyceride and behenoyl monoglyceride. In an embodiment the behenoyl monoglyceride is a mixture of monobehenate and glycerides of shorter fatty acyl chain lengths. In an embodiment at least 85% of the mixture is the monobehenate ester.

In an embodiment the formulation may further comprise an oil which is caprylic/capric triglyceride, a phospholipid which is phosphatidylcholine (as a mixture of C16 and C18 saturated acyl chains), and water. In an embodiment, the formulation may further comprise pentylene glycol, glycerin and gelling agents, an optionally other dermatologically acceptable excipients.

Another aspect of the invention is a method for maintaining the skin barrier efficiency of a patient in need thereof, comprising applying to the skin of said patient a pharmaceutical or cosmetic formulation containing at least 0.1 to about 10% w/w of one or more of a monofatty acid ester of glycerin and/or one or more of a monofatty acid ester of glycol, or mixtures thereof. In one embodiment, the amount of the one or more of a monofatty acid ester of glycerin and/or one or more of a monofatty acid ester of glycol, or mixtures thereof in the formulation is >3% w/w. In another embodiment, the amount of is >5% w/w.

In an embodiment the formulation may further comprise an oil which is caprylic/capric triglyceride, a phospholipid which is phosphatidylcholine (as a mixture of C16 and C18 saturated acyl chains), and water. In an embodiment, the formulation may further comprise pentylene glycol, glycerin and gelling agents, an optionally other dermatologically acceptable excipients.

Another aspect of the invention is a method for improving the occlusiveness of a pharmaceutical or cosmetic formulation in use in a patient in need thereof, comprising adding to the formulation at least 0.1 to about 10% w/w of one or more of a monofatty acid ester of glycerin and/or one or more of a monofatty acid ester of glycol, or mixtures thereof. In one embodiment, the amount of the one or more of a monofatty acid ester of glycerin and/or one or more of a monofatty acid ester of glycol, or mixtures thereof in the formulation is >3% w/w. In another embodiment, the amount of is >5% w/w. In an embodiment, the ethyleneglycol monoglyceride is a mixture of ethylene glycol monoglyceride and behenoyl monoglyceride. In an embodiment the behenoyl monoglyceride is a mixture of monobehenate and glycerides of shorter fatty acyl chain lengths. In an embodiment at least 85% of the mixture is the monobehenate ester.

In an embodiment the formulation may further comprise an oil which is caprylic/capric triglyceride, a phospholipid which is phosphatidylcholine (as a mixture of C16 and C18 saturated acyl chains), and water. In an embodiment, the formulation may further comprise pentylene glycol, glycerin and gelling agents, an optionally other dermatologically acceptable excipients.

On aspect of the invention is a topical oil-in-water emulsion composition comprising
  a) a discontinuous oil phase;
  b) a continuous aqueous phase comprising water;
  c) a thickening agent;
  d) one or more of a monofatty acid ester of glycerin and/or one or more of a monofatty acid ester of glycol, or mixtures thereof; and
  e) at least one lamellar membrane structure comprising (i) a phospholipid; and ii) a fatty alcohol;
wherein in use the composition has a water vapor transmission rate measured in vitro using the modWVTR test methodology that is less than a composition not containing a monofatty acid ester of glycerin and/or a monofatty acid ester of glycol.

In an embodiment, the composition has a water vapor transmission rate of less than about 70 $g \cdot m^{-2} \cdot hr^{-1}$ measured in vitro using the modWVTR test methodology. In another embodiment, the composition has a water vapor transmission rate of less than about 65 $g \cdot m^{-2} \cdot hr^{-1}$ measured in vitro using the modWVTR test methodology. In another embodiment, the composition has a water vapor transmission rate of less than about 60 g·m$^{-2}$·hr$_{-1}$ measured in vitro using the modWVTR test methodology.

In one embodiment, the composition is free from an anionic surfactant and/or a ceramide. In another embodiment, the composition is free from or substantially free from conventional surfactants. In yet another embodiment, the composition is free from or substantially free from conventional surfactants and from ceramides.

DETAILED DESCRIPTION OF THE INVENTION

On aspect of the invention is a topical oil-in-water emulsion composition comprising
- a) a discontinuous oil phase;
- b) a continuous aqueous phase comprising water;
- c) a thickening agent;
- d) one or more of a monofatty acid ester of glycerin and/or one or more of a monofatty acid ester of glycol, or mixtures thereof; and
- e) at least one lamellar membrane structure comprising (i) a phospholipid; ii) a fatty alcohol and (ii) a fatty acid;

wherein in use the composition has a water vapor transmission rate measured in vitro using the modWVTR test methodology that is less than a composition not containing a monofatty acid ester of glycerin and/or a monofatty acid ester of glycol.

On aspect of the invention is a topical oil-in-water emulsion composition comprising
- a) a discontinuous oil phase;
- b) a continuous aqueous phase comprising water;
- c) a thickening agent;
- d) one or more of a monofatty acid ester of glycerin and/or one or more of a monofatty acid ester of glycol, or mixtures thereof; and
- e) at least one lamellar membrane structure comprising (i) a phospholipid; ii) a fatty alcohol, (iii) a fatty acid and (iv) a fatty ester;

wherein in use the composition has a water vapor transmission rate measured in vitro using the modWVTR test methodology that is less than a composition not containing a monofatty acid ester of glycerin and/or a monofatty acid ester of glycol.

The structure of SC has been described as a 'brick wall' structure where the bricks refer to the corneocytes and the mortar between the bricks is the lipid-rich matrix. This lipid matrix contains mainly ceramides, cholesterol, and fatty acids of varying chain lengths (C16-C26)-(See K. P. Ananthapadmanabhan, et al. International Journal of Cosmetic Science, 35 (2013) 337-345). These molecules organize themselves in two lamellar phases; namely the Long Periodicity Phase (LPP) and Short Periodicity Phase (SPP). The LPP and SPP are approximately 13 nm and 6 nm in thickness, respectively, as determined by X-ray diffraction (J. A. Bouwstra, Open Dermatology Journal, 4 (2010) 10-13). Moreover, perpendicular to the lamellar phase SC lipids organize in orthorhombic, hexagonal and/or fluid packed lamellar structures.

Healthy skin lipids are predominantly organized in an orthorhombic packing state, the significance of which is that the tighter packing behavior and higher level of organization of SC lipids results in a lower transepidermal water loss (TEWL) and improved barrier properties (See F. Damien, et al., J Invest Dermatol, 130 (2009) 611-614; G. S. Pilgram, et al., J Invest Dermatol, 113 (1999) 403-409; D. Groen, et al., Biochim Biophys Acta, 1808 (2011) 1529-1537). However, in skin diseases such as atopic dermatitis and xerosis, hexagonal phases are known to be present at higher levels than in healthy skin, driven partly by a reduction in the chain length of the fatty acids and ceramides, in the SC. (See G. S. Pilgram, et al., J Invest Dermatol, 117 (2001) 710-717; M. Janssens, et al., J Invest Dermatol, 131 (2011) 2136-2138; M. Janssens, et al., J Lipid Res, 53 (2012) 2755-2766; and A. W. Fulmer et al., J Invest Dermatol, 86 (1986) 598-602).

Long chain fatty acids have been shown to play a fundamental role in maintaining skin barrier efficiency. A particular long chain fatty acid, behenic acid, was investigated further and different behenoyl lipids have been synthesized and fractionated from Compritol ATO 888, and evaluated as assisting in lipids barrier protection.

Differential scanning calorimetry showed higher melting points for glycerides containing a single fatty acyl chain. This suggests better molecular packing as compared with their di- and tri-glyceride counterparts. Fourier transform infrared spectroscopy confirmed better conformational ordering with the presence of an orthorhombic lipid phase for the mono- and di-glycerides. Furthermore, Langmuir monolayer studies also demonstrated improved packing characteristics for both synthesized and fractionated behenoyl monoglyceride while atomic force microscopy imaging has validated the presence of a homogeneous monolayer for the monoglycerides.

Finally, the results of water vapor transmission rate (WVTR) studies further demonstrated that mono-glycerides formulated at 3% w/w presents an occlusive film comparable to that of 10% w/w of petrolatum, and was significantly superior to a 3% w/w petrolatum formulation.

Results also show that the acylation of monoglycerides decreases the tightness of lateral packing and reduces occlusivity as measured by WVTR suggesting the importance of hydrogen bonding on molecular bulk to form good occlusive films. Unexpectantly, the mono single fatty acyl chain is shown to provide better water vapor transmission rates (WVTR) as compared with its di- and tri-glyceride counterpart.

Lipid mixtures containing mainly glycerol monobehenate (C22 approximately 88% along with shorter acyl chain variants) displayed lower WVTR values than the corresponding pure synthetic Compound 1 (C22>96%) indicating that the additional lipids help in forming better barriers. This data supports the conclusion that behenoyl monoglycerides form an occlusive orthorhombic mesophase similar to that of skin lipids. Thus, behenoyl monoglyceride can be incorporated into skin moisturizers and can be used to provide occlusive and highly structured lipids as herein described.

One embodiment of the invention is the use of one or more of a monofatty acid ester of glycerin and/or one or more of a monofatty acid ester of glycol, or mixtures thereof to improve the occlusiveness of formulations that incorporate it. Suitably, the mono-fatty acid ester of glycerin is behenoyl monoglyceride or a mixture of behenoyl monoglyceride and other monofatty acid esters of glycerin, such as the fractionated glycerol monobehenate (FGMB) described herein.

Another embodiment is the use of one or more of a monofatty acid ester of glycerin and/or one or more of a monofatty acid ester of glycol, or mixtures thereof for improving skin surface moisturization in the stratum corneum.

Another embodiment is the use of one or more of a monofatty acid ester of glycerin and/or one or more of a monofatty acid ester of glycol, or mixtures thereof to improve surface textural properties of the stratum corneum.

Glycerin, often used as a humectant in moisturizing formulations, not only helps to absorb water but also seems to modulate SC lipid packing behavior possibly by enabling the lipids to preserve liquid crystal phase at low humidity. The increased SC hydration then leads to enhanced SC desquamation and relief of dry skin. Alternatively, pentylene glycol alone or in combination with glycerin may similarly play a role in assisting with lateral packing. Long chain fatty acids are known to be depleted from SC lipids in dry skin and have been demonstrated to play a crucial role in maintaining the orthorhombic packing of these lipids. Mixtures of ceramide/cholesterol/fatty acid containing predominantly C16 and C18 carbon chain fatty acid do not display orthorhombic packing. The use of glycerol monobehenate and/or other long chain monoglycerides differs from the traditional skin care formulation in that it is not linked to a ceramide, cholesterol or sphingosine molecule.

Another aspect of the present invention is inclusion of one or more of a monofatty acid ester of glycerin and/or one or more of a monofatty acid ester of glycol, or mixtures thereof in a topical oil-in-water emulsion composition having enhanced occlusiveness.

On aspect of the invention is a topical oil-in-water emulsion composition comprising
  a) a discontinuous oil phase;
  b) a continuous aqueous phase comprising water;
  c) a thickening agent;
  d) one or more of a monofatty acid ester of glycerin and/or one or more of a monofatty acid ester of glycol, or mixtures thereof; and
  e) at least one lamellar membrane structure comprising (i) a phospholipid; and ii) a fatty alcohol;
wherein in use the composition has a water vapor transmission rate measured in vitro using the modWVTR test methodology that is less than a composition not containing a monofatty acid ester of glycerin and/or a monofatty acid ester of glycol.

In one embodiment, the composition is free from an anionic surfactant and/or a ceramide. In another embodiment, the composition is free from or substantially free from conventional surfactants. In yet another embodiment, the composition is free from or substantially free from conventional surfactants and from ceramides.

In an embodiment, the composition the lamellar membrane structure comprises a phospholipid suitably selected from the group consisting of lecithin, hydrogenated lecithin, phosphatidylcholine, hydrogenated phosphatidylcholine, and mixtures thereof. In an embodiment, the phospholipid is hydrogenated phosphatidylcholine.

In one embodiment, the phospholipid is lecithin. In another embodiment, the phospholipid is hydrogenated lecithin. In yet another embodiment, the phospholipid is phosphatidylcholine. In a further embodiment, the phospholipid is hydrogenated phosphatidylcholine.

One suitable source of phosphatidylcholine is phospholipon 90H. In an embodiment, the phosphatidylcholine is present as a mixture of $C_{16}$ and $C_{18}$ saturated acyl chains.

As used herein, "phosphatidylcholine" (PC) is a class of phospholipids that incorporate choline as a headgroup. Purified phosphatidylcholine is produced commercially. Phosphatidylcholines may be from any source, such as soy or egg. Soy phosphatidylcholine is characterized by a proportion of linoleic acid up to 70% of the total fatty acids. Egg phosphatidylcholine contains 28-38% palmitic acid, 9-18% stearic acid, 25-37% oleic acid, 12-17% linoleic acid, about 0.5% linolenic acid and 1-7% arachidonic acid. The phospholipids herein may also include hydrogenated PC's, such as soy phosphatidylcholine which contains mainly stearic and palmitic acids, and semisynthetic compounds such as dipalmitoyl phosphatidylcholine and distearoyl phosphatidylcholine. By way of clarification, it is to be noted that the term phospholipid covers not only a single phospholipid but also a mixture of phospholipids, wherein the phospholipid or respectively the phospholipid mixture can be of natural or synthetic origin. It is likewise self-evident that the phospholipid can be hydrogenated, but that instead of this hydrogenated phospholipid a synthetic phospholipid can be used, e.g. in which the acyl radicals are all or predominantly saturated in the above sense.

In one embodiment of the disclosure, the hydrogenated phosphatidylcholine is at least 60% by weight hydrogenated PC.

In an embodiment, the phospholipid is present in an amount from about 0.5% to about 5% by weight, based on the total weight of the composition. In another embodiment, the phospholipid is present in an amount from about 0.5% to about 2.5% by weight, based on the total weight of the composition.

In an embodiment, the lamellar membrane structure comprises a fatty alcohol. The fatty alcohol is a branched or straight chain $C_{12}$-$C_{36}$ fatty alcohol which may be saturated or unsaturated. In another embodiment, the fatty alcohol is a branched or straight chain $C_{14}$-$C_{26}$ fatty alcohol. In another embodiment, the fatty alcohol is a branched or straight chain $C_{16}$ to $C_{22}$ fatty alcohol. In another embodiment, the fatty alcohol is a a branched or straight chain $C_{20}$-$C_{26}$ fatty alcohol. In another, the branched or straight chain is $C_{18}$-$C_{30}$ carbon atoms. In yet another embodiment, the branched or straight chain is $C_{20}$ to $C_{30}$ carbon atoms. In a further embodiment, the branched or straight chain is $C_{22}$ to $C_{28}$ carbon atoms. In another embodiment, the fatty alcohol is a $C_{18}$ or $C_{22}$ or $C_{24}$ branched or straight chain fatty alcohol. In yet another embodiment, the fatty alcohol is a $C_{18}$ or $C_{22}$ or $C_{24}$ branched fatty alcohol. In another embodiment, the fatty alcohol is a branched chain fatty alcohol. In another embodiment, the fatty alcohol is a straight chain fatty alcohol. In an embodiment, the fatty alcohol is a mixture of two or more fatty alcohols.

Exemplary straight chain fatty alcohols for use in the invention include, but are not limited to, decyl alcohol ($C_{10}$), lauryl alcohol ($C_{12}$), tridecyl alcohol ($C_{13}$), myristyl alcohol ($C_{14}$), pentadecyl alcohol ($C_{15}$), cetyl alcohol ($C_{16}$), cetearyl alcohol ($C_{16}$/$C_{18}$), palmitoleyl alcohol ($C_{16}$), heptadecyl alcohol ($C_{17}$), stearyl alcohol ($C_{18}$), nonadecyl alcohol ($C_{19}$), arachidyl alcohol ($C_{20}$), heneicosyl alcohol ($C_{21}$), behenyl alcohol ($C_{22}$), erucyl alcohol ($C_{22}$), lignoceryl alcohol ($C_{24}$), ceryl alcohol ($C_{26}$), 1-heptacosanol ($C_{27}$), montanyl alcohol ($C_{28}$), 1-nonacosanol ($C_{29}$), myricyl alcohol ($C_{30}$), lacceryl alcohol ($C_{32}$), geddyl alcohol ($C_{34}$) and tetratriacontanol ($C_{36}$), and mixtures thereof.

In one embodiment, the fatty alcohols include, but are not limited to, behenyl alcohol, isostearyl alcohol, caprylyl alcohol, decyl alcohol, lauryl alcohol, myristyl alcohol, lanolin alcohol, lignoceryl alcohol, arachidyl alcohol, oleyl alcohol, palm alcohol, isocetyl alcohol, cetyl alcohol, stearyl alcohol and cetearyl alcohol, and mixtures thereof.

In an embodiment, the straight chain fatty alcohol is cetyl alcohol ($C_{18}$).

In one embodiment, the straight chain fatty alcohol is behenyl alcohol ($C_{22}$).

In another embodiment, the straight chain fatty alcohol is a mixture of cetyl alcohol ($C_{16}$) and behenyl alcohol ($C_{22}$).

In an embodiment, the fatty alcohol is present in an amount from about 2% to about 15% by weight, based on the total weight of the composition. In another embodiment, the fatty alcohol is present in an amount from about 2% to about 10% by weight, or from about 2% to about 7.5% by weight, based on the total weight of the composition.

In an embodiment, the fatty alcohol and the phospholipid are present in a weight ratio from about 10:1 to about 1:1. In one embodiment, the fatty alcohol and the phospholipid are present in a weight ratio from about 8:1 to about 2:1. In another embodiment, the fatty alcohol and the phospholipid are present in a weight ratio from about 5:1 to about 4:1.

In an embodiment, the lamellar membrane structure comprises, or further comprises a fatty acid. In an embodiment, the fatty acid is a mixture of two or more fatty acids.

In one embodiment, the fatty acid is a $C_{12}$ to $C_{36}$ fatty acid which may be saturated or unsaturated, branched or straight chained. In one embodiment, the branched or straight chain is $C_{16}$-$C_{26}$ carbon atoms. In another embodiment the branched or straight chain is $C_{12}$-$C_{22}$ carbon atoms. In an embodiment, the fatty acid is a $C_{18}$ to $C_{36}$ fatty acid. In another, the branched or straight chain is $C_{18}$-$C_{30}$ carbon atoms. In yet another embodiment, the branched or straight chain is $C_{20}$-$C_{30}$ carbon atoms. In yet another embodiment, the branched or straight chain is $C_{20}$-$C_{28}$ carbon atoms. In another embodiment, the fatty acid is a $C_{20}$ to $C_{26}$ fatty acid. In yet another embodiment, the branched or straight chain is $C_{22}$-$C28_{30}$ carbon atoms. In yet another embodiment, the fatty acid is a $C_{22}$ or $C_{24}$ fatty acid. In an embodiment, the fatty acid is present in an amount from about 0.1% to about 5% by weight, based on the total weight of the composition.

In one embodiment, the fatty acid is a straight chain fatty acid.

In an embodiment, the straight chain fatty acid is a $C_{12}$ to $C_{30}$ straight chain fatty acid. In another embodiment, the straight chain fatty acid is a $C_{18}$-$C_{30}$ straight chain fatty acid. In yet another embodiment, the straight chain fatty acid is a $C_{20}$-$C_{30}$ straight chain fatty acid. In a further embodiment, the straight chain fatty acid is a $C_{20}$-$C_{26}$ straight chain fatty acid. In yet a further embodiment, the straight chain fatty acid is a $C_{22}$ or $C_{24}$ straight chain fatty acid. Exemplary straight chain fatty acids for use in the lamellar membrane structure include, but are not limited to, lauric acid ($C_{12}$), tridecylic acid ($C_{13}$), myristic acid ($C_{14}$), pentadecylic acid ($C_{15}$), palmitic acid ($C_{16}$), margaric acid ($C_{17}$), stearic acid ($C_{18}$), nonadecylic acid ($C_{19}$), arachidic acid ($C_{20}$), heneicosylic acid ($C_{21}$), behenic acid ($C_{22}$), tricosylic acid ($C_{23}$), lignoceric acid ($C_{24}$), pentacosylic acid ($C_{25}$), cerotic acid ($C_{26}$), heptacosylic acid ($C_{27}$), montanic acid ($C_{28}$), nonacosylic acid ($C_{29}$), melissic acid ($C_{30}$), henatriacontylic acid ($C_{31}$), lacceroic acid ($C_{32}$), psyllic acid ($C_{33}$), geddic acid ($C_{34}$), ceroplastic acid ($C_{35}$) and hexatriacontylic acid ($C_{36}$), and mixtures thereof.

In one embodiment, the straight chain fatty acid is behenic acid ($C_{22}$).

Other exemplary fatty acids include, but are not limited to, isostearic acid (also known as isoactadecanoic acid) (C18), linoleic acid (C18), linolenic acid (C18), oleic acid (C18), myristic acid (also known as tetradecanoic acid) (C14), ricinoleic acid (C18), columbinic acid (C18), arachidic acid (also known as eicosanoic acid) (C20), arachidonic acid (C20), lignoceric acid (also known as tetracosanoic acid) (C24), nervonic acid (C24), eicosapentanoic acid (C20), palmitic acid (also known as hexadecanoic acid) (C16), and mixtures thereof.

Fatty acids suitable for use herein can be obtained from natural sources. For example, the fatty acids may be obtained from palm oil, rape seed oil, palm kernel oil, coconut oil, babassu oil, soybean oil, castor oil, sunflower oil, olive oil, linseed oil, cottonseed oil, safflower oil, tallow, whale or fish oils, and mixtures thereof. The fatty acids can also be synthetically prepared. Fatty acids can also be prepared from mixtures of natural or synthetic wax esters by use of appropriate synthetic chemistry. Examples include Rice Bran Wax, etc.

In another embodiment, the fatty acid is present in an amount from about 0.1% to about 5% by weight, based on the total weight of the composition. In another embodiment, the fatty acid is present in an amount from about 0.25% to about 2.5% by weight, or from about 0.5% to about 2.5% by weight, based on the total weight of the composition.

In an embodiment, the fatty alcohol and the fatty acid are present in a weight ratio from about 10:1 to about 1:1. In one embodiment, the fatty alcohol and the fatty acid are present in a weight ratio from about 8:1 to about 4:1.

In an embodiment, the phospholipid and fatty acid are present in a weight ratio from about 5:1 to about 1:5. In one embodiment, the fatty acid and phospholipid are present in a weight ratio from about 2:1 to about 1:2. In another embodiment, the phospholipid and the fatty acid are present in a weight ratio from about 2:1 to about 1:1.

In an embodiment the lamellar membrane structure further comprises an ester of a branched fatty acid and a branched fatty alcohol.

In an embodiment, the ester comprises a mixture of compounds having mono- and poly-branching in the acid and alcohol originating parts of the ester. In one embodiment, the fatty acid and fatty alcohol are alkyl branched.

In an embodiment, the branched fatty acid component of the ester is a $C_{12}$ to $C_{36}$ branched fatty acid, a $C_{12}$ to $C_{30}$ branched fatty acid, a $C_{14}$ to $C_{26}$ branched fatty acid, a $C_{16}$ to $C_{22}$ branched fatty acid, or a $C^{18}$ branched fatty acid.

In another embodiment, the ester is an ester of a $C_{16}$ to $C_{30}$ branched fatty acid and a $C_{16}$ to $C_{30}$ branched fatty alcohol. In another embodiment, the ester is isostearyl isostearate. In one embodiment the ester is present in an amount from about 0.1% to about 5% by weight, based on the total weight of the composition.

Fatty acids suitable for use in the ester can be obtained from natural sources or can also be synthetically prepared. For example, the fatty acids may be obtained from palm oil, rape seed oil, palm kernel oil, coconut oil, babassu oil, soybean oil, castor oil, sunflower oil, olive oil, linseed oil, cottonseed oil, safflower oil, tallow, whale or fish oils, grease, lard and mixtures thereof. Or they could have come from mixtures of wax esters that have been modified to be predominantly fatty acid mixtures (ester hydrolysis). The fatty acids can also be synthetically prepared. Relatively pure unsaturated fatty acids such as oleic acid, linoleic acid, linolenic acid, palmitoleic acid, and elaidic acid may be isolated, or relatively crude unsaturated fatty acid mixtures may be used as a basis for chemical modification.

Exemplary branched fatty acids for use in the ester include, but are not limited to, iso-acids such as isostearic acid, isopalmitic acid, isomyristic acid, isoarachidic acid and isobehenic acid, neo-acids such as neodecanioc acid, and/or anti-iso acids. In one embodiment, the branched fatty acid for use in the ester is isostearic acid.

In an embodiment, the branched fatty alcohol component of the ester is a $C_{12}$ to $C_{36}$ branched fatty alcohol, a $C_{12}$ to $C_{30}$ branched fatty alcohol, a $C_{14}$ to $C_{26}$ branched fatty alcohol, a $C_{16}$ to $C_{22}$ branched fatty alcohol, or a $C_{18}$ branched fatty alcohol.

In another embodiment, the ester is an ester of a $C_{16}$ to $C_{22}$ branched fatty acid and a $C_{16}$ to $C_{22}$ branched fatty alcohol. The branched fatty acid and branched fatty alcohol may comprise the same number of carbon atoms, or a different number of carbon atoms. In one embodiment, the branched fatty acid and branched fatty alcohol comprise the same number of carbon atoms.

The ester may comprise one or more variations selected from the group comprising mono-branched fatty acid and poly-branched fatty alcohol, mono-branched fatty acid and mono-branched fatty alcohol, poly-branched fatty acid and mono-branched fatty alcohol, and poly-branched fatty acid and poly-branched fatty alcohol. The ester may be selected from this group by any suitable separation method. For example, the selected ester may be selected from a mixture of esters using a clathration method.

Exemplary branched fatty alcohols for use in the ester include, but are not limited to, iso-alcohols such as isostearyl alcohol, isotetradecanol, isocetyl alcohol, isoarachidyl alcohol, isobehenyl alcohol and isolignoceryl alcohol; neo-alcohols such as neocapric alcohol; and/or anti-iso alcohols. In one embodiment, the fatty alcohol for use in the ester is isostearyl alcohol.

In an embodiment, the ester is isostearyl isostearate ("ISIS").

Exemplary branched fatty alcohols for use in the ester include, but are not limited to, iso-alcohols such as isostearyl alcohol, isotetradecanol, isocetyl alcohol, isoarachidyl alcohol, isobehenyl alcohol and isolignoceryl alcohol; neo-alcohols such as neocapric alcohol; and/or anti-iso alcohols. In one embodiment, the fatty alcohol for use in the ester is isostearyl alcohol.

Suitably, the ester is present in the lamellar membrane blend in an amount from about 1% to about 75% by weight, preferably from about 5% to about 50% by weight, more preferably from about 5% to about 35% by weight, based on the total weight of the lamellar membrane blend. In one embodiment, the ester is present in the lamellar membrane blend in an amount from about 1% to about 25% by weight, based on the total weight of the lamellar membrane blend.

In an embodiment, the phospholipid and the ester are present in a weight ratio from about 5:1 to about 1:5. In another embodiment, the phospholipid and ester are present in a weight ratio from about 2:1 to about 1:2. In yet another embodiment, the phospholipid and ester are present in a weight ratio from about 2:1 to about 1:1.

In an embodiment, the fatty alcohol and the ester are present in a weight ratio from about 10:1 to about 1:1. In another embodiment, the fatty alcohol and the ester are present in a weight ratio from about 8:1 to about 4:1.

In an embodiment, the fatty acid and the ester are present in a weight ratio from about 5:1 to about 1:5. In yet another embodiment, the fatty acid and the ester are present in a weight ratio from about 2:1 to about 1:2. In a further embodiment, the fatty acid and the ester are present at a weight ratio of about 1:1.

In an embodiment, the ester is present in an amount from about 0.1% to about 5% by weight, based on the total weight of the composition. In one embodiment, the ester is present in an amount from about 0.25% to about 2.5% by weight, or from about 0.5% to about 2.5% by weight, based on the total weight of the composition.

In a further embodiment, the weight ratio of phospholipid:fatty alcohol:fatty acid:ester is about 1.4:6.4:1:1.

In one embodiment, the one or more of a mono fatty acid ester of glycerin and/or the one or more of a mono fatty acid ester of glycol are one or more of a mono $C_{10}$-$C_{36}$ fatty acid ester of glycerin or glycol, or mixtures thereof. As used herein the term "one or more of" implies a mono fatty acid ester of glycerin or a mixture of mono fatty acid esters of glycerin, or a mono fatty acid ester of glycol or a mixture of mono fatty acid esters of glycol.

In one embodiment, the one or more mono fatty acid esters of glycerin or glycol are $C_{16}$-$C_{36}$ straight or branched carbon chains, and may be saturated or unsaturated. In another embodiment, the one or more mono fatty acid esters of glycerin or glycol are $C_{18}$-$C_{36}$ straight or branched carbon chains. In another embodiment, the mono fatty acid esters of glycerin or glycol are $C_{22}$-$C_{36}$ straight or branched carbon chains. In another embodiment, the mono fatty acid esters of glycerin or glycol are $C_{18}$-$C_{26}$ straight or branched carbon chains. In one embodiment, the fatty acid forming the ester is suitably selected from a C23-C28.

Suitably, the one or more mono fatty acid ester of glycerin and/or the one or more mono fatty acid ester of glycol include but are not limited to behenoyl monoglyceride, ethyleneglyol monobehenate, or mixtures thereof.

Exemplary fatty acids for use in making the mono esters or glycerin or glycol include, but are not limited to, isostearic acid (also known as isoactadecanoic acid) (C18), linoleic acid (C18), linolenic acid (C18), oleic acid (C18), myristic acid (also known as tetradecanoic acid) (C14), ricinoleic acid (C18), columbinic acid (C18), arachidic acid (also known as eicosanoic acid) (C20), arachidonic acid (C20), heneicosic acid ($C_21$), erucic acid ($C_{22}$), lignoceric acid (also known as tetracosanoic acid) (C24), nervonic acid (C24), ceric acid ($C_{26}$), montanic acid ($C_{28}$), nonacosanoic acid ($C_{29}$), lacceric acid ($C_{32}$), geddic acid ($C_{34}$) and tetratriacontanol (C36), eicosapentanoic acid (C20), palmitic acid (also known as hexadecanoic acid) (C16), stearic acid (also known as octadecanoic acid) (C18), behenic acid (also known as docosanoic acid)(C22), heptacosenoic acid (C27), nonacosanoic acid (C29), tricontanoic acid (C30), and mixtures thereof.

In an embodiment, the one or more mono fatty acid ester of glycerin and/or the one or more mono fatty acid ester of glycol, or mixtures thereof is present in the composition in an amount from about 0.1 to about 10% by weight, based on the total weight of the composition. In one embodiment, the amount of the one or more mono fatty acid ester of glycerin and/or the one or more mono fatty acid ester of glycol, or mixtures thereof present in the composition is >3% w/w. In another embodiment, the amount of the one or more mono fatty acid ester of glycerin and/or the one or more mono fatty acid ester of glycol, or mixtures thereof is >5% w/w.

For purposes herein, glycerol mono behenate is also referred to as behenoyl monoglyceride. In one embodiment, the behenoyl monoglyceride is present as a mixture of monobehenate and glycerides of shorter or longer fatty acyl chain lengths. In another embodiment, at least 85% of this mixture is the monobehenate ester. The mixture may also include isomers of the glyceride monoester.

In one embodiment, the lamellar membrane structure comprises phosphatidylcholine present as a mixture of $C_{16}$ and $C_{18}$ saturated acyl chains. In another embodiment, the composition further comprises caprylic/capric triglyceride. In another embodiment, the lamellar membrane structure comprises caprylic/capric triglyceride, phosphatidylcholine present as a mixture of $C_{16}$ and $C_{18}$ saturated acyl chains, a fatty alcohol which is a $C_{12}$-$C_{36}$ fatty alcohol. In another embodiment, the lamellar membrane structure comprises caprylic/capric triglyceride, phosphatidylcholine present as a mixture of $C_{16}$ and $C_{18}$ 8 saturated acyl chains, a fatty alcohol which is a $C_{12}$-$C_{36}$ fatty alcohol, and a $C_{12}$ to $C_{36}$ fatty acid. In another embodiment, the lamellar membrane structure comprises caprylic/capric triglyceride, phosphatidylcholine present as a mixture of $C_{16}$ and $C_{18}$ saturated acyl chains, a fatty alcohol which is a $C_{12}$-$C_{36}$ fatty alcohol, a $C_{12}$ to $C_{36}$ fatty acid, and an ester of a branched fatty acid and a branched fatty alcohol In another embodiment, the composition further comprises pentylene glycol, glycerin and gelling agents, an optionally other dermatologically acceptable excipients.

In an embodiment, there is a method for moisturizing, and protecting, repairing, or restoring the skin lipid barrier of a mammal, the method comprising applying to the skin of the mammal in need thereof an effective amount of a topical oil-in-water emulsion composition comprising:
 a) a discontinuous oil phase;
 b) a continuous aqueous phase comprising water;
 c) a thickening agent;
 d) one or more mono fatty acid esters of glycerin and/or the one or more mono fatty acid esters of glycol, or mixtures thereof; and
 e) at least one lamellar membrane structure comprising (i) a phospholipid; and (ii) a fatty alcohol;
wherein in use the composition has a water vapor transmission rate measured in vitro using the modWVTR test methodology that is less than a composition not containing a monofatty acid ester of glycerin and/or a monofatty acid ester of glycol.

Another aspect of the invention is a topical oil-in-water emulsion composition comprising
 a) a discontinuous oil phase;
 b) a continuous aqueous phase comprising water;
 c) a thickening agent;
 d) one or more of a monofatty acid ester of glycerin and/or one or more of a monofatty acid ester of glycol, or mixtures thereof; and
 e) at least one lamellar membrane structure comprising (i) a phospholipid; and ii) a fatty alcohol;
wherein in use the composition has a water vapor transmission rate measured in vitro using the modWVTR test methodology that is less than a composition not containing a monofatty acid ester of glycerin and/or a monofatty acid ester of glycol for use in protecting, repairing, or restoring the skin lipid barrier of a mammal.

Another embodiment of the disclosure is the use of a of a topical oil-in-water emulsion composition comprising:
 a) a discontinuous oil phase;
 b) a continuous aqueous phase comprising water;
 c) a thickening agent;
 d) one or more mono fatty acid ester of glycerin and/or the one or more mono fatty acid ester of glycol, or mixtures thereof; and
 e) at least one lamellar membrane structure comprising (i) a phospholipid; (ii) a fatty alcohol; and (iii) a fatty acid;
wherein in use the composition has a water vapor transmission rate measured in vitro using the modWVTR test methodology that is less than a composition not containing a monofatty acid ester of glycerin and/or a monofatty acid ester of glycol, in the manufacture of a cosmetic or pharmaceutical composition for moisturizing, and protecting, repairing, or restoring the skin lipid barrier of a mammal.

In all of these methods the same embodiments of the composition as noted above apply to the respective uses.

The composition may further comprise at least one dermatologically acceptable excipient selected from an antioxidant, a chelating agent, a preservative, a colorant, a sensate, a moisturizer, a humectant, and a pH adjusting agent, and mixtures thereof.

In one embodiment, the lamellar membrane structure composition comprises a phospholipid, a fatty alcohol, and optionally a fatty acid and/or an ester of a branched fatty acid and a branched fatty alcohol. The lamellar membrane structure may further comprise an additional oil/lipid (as herein defined for the oil phase), in addition to the discontinuous oil phase. The oil may be the same or different than the oil present in the discontinuous oil phase. In one embodiment, additional oil is selected from a squalane, a phytosterol, cholesterol or cholesterol derivative, a triglyceride, rice bran oil, or rice bran wax, and mixtures thereof. In one embodiment the lipid is a triglyceride. In another embodiment, the lipid is caprylic/capric/triglyceride.

Oil Phase

The compositions comprise a discontinuous oil phase. The discontinuous oil phase is dispersed throughout the continuous aqueous phase.

In an embodiment, the discontinuous oil phase comprises at least one oil and/or fat. For purposes herein oil, lipid and fat are used interchangeably. In one embodiment, the oil and/or fat is a mixture of two or more oils and/or fats. Exemplary oils and fats include, but are not limited to, fatty acids, fatty alcohols, esters, esters of glycerin, waxes, sterols, essential oils, vegetable oils and edible oils, and mixtures thereof.

In an embodiment, the at least one oil and/or fat is a fatty acid which may be saturated or unsaturated, branched or straight chained. In an embodiment, the fatty acid is a mixture of two or more fatty acids.

In an embodiment, the fatty acid is a $C_{12}$-$C_{36}$ fatty acid which may be saturated or unsaturated, branched or straight chained. In one embodiment, the branched or straight chain is $C_{16}$-$C_{26}$ carbon atoms. In another embodiment the branched or straight chain is $C_{12}$-$C_{22}$ carbon atoms. In another, the branched or straight chain is $C_{18}$-$C_{36}$ carbon atoms. In another, the branched or straight chain is $C_{18}$-$C_{30}$ carbon atoms. In another embodiment, the branched or straight chain is $C_{20}$-$C_{30}$ carbon atoms. In yet another embodiment, the branched or straight chain is $C_{20}$-$C_{28}$ carbon atoms. In a further embodiment, the branched or straight chain is $C_{20}$-$C_{26}$ carbon atoms. In a further embodiment, the branched or straight chain is $C_{22}$-$C_{28}$ carbon atoms. In yet another embodiment, the branched or straight chain is $C_{22}$-$C_{30}$ carbon atoms. In yet a further embodiment, the fatty acid is a branched or straight $C_{22}$ or a $C_{24}$ chain.

In one embodiment, the fatty acid is a straight chain fatty acid. In one embodiment, the fatty acid is an unsaturated straight chain fatty acid.

In an embodiment, the straight chain fatty acid is a $C_{12}$ to $C_{36}$ straight chain fatty acid. In an embodiment, the straight chain fatty acid is a $C_{16}$ to $C_{36}$ straight chain fatty acid. In another embodiment, the straight chain fatty acid is a $C_{12}$-$C_{22}$ straight chain fatty acid. In an embodiment, the straight chain fatty acid is a $C_{18}$ to $C_{36}$ straight chain fatty acid. In an embodiment, the straight chain fatty acid is a $C_{18}$ to $C_{30}$ straight chain fatty acid. In yet another embodiment, the straight chain fatty acid is a $C_{20}$-$C_{30}$ straight chain fatty acid. In a further embodiment, the straight chain fatty acid is a $C_{20}$-$C_{28}$ straight chain fatty acid. In an embodiment, the straight chain fatty acid is a $C_{20}$ to $C_{26}$ straight chain fatty acid. In yet a further embodiment, the straight chain fatty acid is a $C_{22}$ or a $C_{24}$ straight chain fatty acid.

Exemplary straight chain fatty acids for use in the lamellar membrane structure include, but are not limited to, lauric acid ($C_{12}$), tridecylic acid ($C_{13}$), myristic acid ($C_{14}$), pentadecylic acid ($C_{15}$), palmitic acid ($C_{16}$), margaric acid ($C_{17}$), stearic acid ($C_{18}$), nonadecylic acid ($C_{19}$), arachidic acid ($C_{20}$), heneicosylic acid ($C_{21}$), behenic acid ($C_{22}$), tricosylic acid ($C_{23}$), lignoceric acid ($C_{24}$), pentacosylic acid ($C_{25}$), cerotic acid ($C_{26}$), heptacosylic acid ($C_{27}$), montanic acid ($C_{28}$), nonacosylic acid ($C_{29}$), melissic acid ($C_{30}$), henatriacontylic acid ($C_{31}$), lacceroic acid ($C_{32}$), psyllic acid ($C_{33}$), geddic acid ($C_{34}$), ceroplastic acid ($C_{35}$) and hexatriacontylic acid ($C_{36}$), and mixtures thereof.

In one embodiment, the straight chain fatty acid is behenic acid ($C_{22}$).

Other exemplary fatty acids include, but are not limited to, isostearic acid (also known as isooctadecanoic acid) (C18), linoleic acid (C18), linolenic acid (C18), oleic acid (C18), myristic acid (also known as tetradecanoic acid) (C14), ricinoleic acid (C18), columbinic acid (C18), arachidic acid (also known as eicosanoic acid) (C20), arachidonic acid (C20), lignoceric acid (also known as tetracosanoic acid) (C24), nervonic acid (C24), eicosapentanoic acid (C20), palmitic acid (also known as hexadecanoic acid) (C16), and mixtures thereof.

In one embodiment, exemplary fatty acids include, but are not limited to, lauric acid, tridecylic acid, myristic acid, pentadecylic acid, palmitic acid, margaric acid, stearic acid, isostearic acid, oleic acid, linoleic acid, linolenic acid, ricinoleic acid, columbinic acid, nonadecylic acid, arachidic acid, arachidonic acid, eicosapentanoic acid, heneicosylic acid, behenic acid, tricosylic acid, lignoceric acid, nervonic acid, pentacosylic acid, cerotic acid, heptacosylic acid, montanic acid, nonacosylic acid, melissic acid, henatriacontylic acid, lacceroic acid, psyllic acid, geddic acid, ceroplastic acid and hexatriacontylic acid, and mixtures thereof.

The fatty acid can be introduced into the present compositions from a variety of sources. In an embodiment, the fatty acid is provided in the composition as an oil or wax. Examples of oils or waxes useful in this regard include, but are not limited to, rice bran oil, rice bran wax, flaxseed oil, hempseed oil, pumpkin seed oil, canola oil, soybean oil, wheat germ oil, olive oil, grapeseed oil, borage oil, evening primrose oil, black currant seed oil, chestnut oil, corn oil, safflower oil, sunflower oil, sunflower seed oil, cottonseed oil, peanut oil, sesame oil and olus (vegetable) oil, including hydrogenated and non-hydrogenated versions thereof, and mixtures thereof. An exemplary wax useful in this regard is rice bran wax.

In one embodiment, the source of fatty acids is shea butter, also known as Butyrospermum parkii, if chemically treated. Shea butter comprises five principal fatty acids, namely palmitic acid, stearic acid, oleic acid, linoleic acid and arachidic acid. Shea butter also comprises phytosterols.

In another embodiment, the at least one oil and/or fat is a fatty alcohol which may be saturated or unsaturated. In one embodiment, the fatty alcohol is suitably a branched or straight chain $C_{12}$-$C_{36}$ fatty alcohol. In one embodiment, the $C_{12}$-$C_{36}$ chain is branched. In another embodiment the $C_{12}$-$C_{36}$ is straight chained. In another embodiment, the fatty alcohol is a branched or straight chain $C_{14}$-$C_{26}$ fatty alcohol. In another embodiment, the fatty alcohol is a branched or straight chain $C_{20}$-$C_{26}$ fatty alcohol. In another embodiment, the fatty alcohol is a branched or straight chain $C_{16}$ to $C_{22}$ fatty alcohol. In one embodiment, the $C_{16}$ to $C_{22}$ chain is branched. In another embodiment, the fatty alcohol is a branched or straight chain $C_{20}$-$C_{26}$ fatty alcohol. In yet another embodiment it is a $C_{18}$ or $C_{22}$ or $C_{24}$ branched or straight chain fatty alcohol. In one embodiment, the $C_{18}$ or $C_{22}$ chain or $C_{24}$ is branched. In yet a further embodiment, the fatty alcohol is a branched or straight $C_{22}$ fatty alcohol. In another embodiment, the fatty alcohol is a branched chain fatty alcohol. In another embodiment, the fatty alcohol is a straight chain fatty alcohol. In an embodiment, the fatty alcohol is a mixture of two or more fatty alcohols.

In one embodiment, the fatty alcohol is a branched chain fatty alcohol. In another embodiment, the fatty alcohol is a straight chain fatty alcohol. The mixture may be a combination of branched, straight, unsaturated and saturated fatty alcohols. In another embodiment, the fatty alcohol is a mixture of at least two fatty alcohols of differing chain lengths.

Exemplary straight chain fatty alcohols for use in the invention include all of those mentioned above under the oil phase and the thickening agents and further include but are not limited to, lauryl alcohol ($C_{12}$), tridecyl alcohol ($C_{13}$), myristyl alcohol ($C_{14}$), pentadecyl alcohol ($C_{15}$), cetyl alcohol ($C_{16}$), cetearyl alcohol ($C_{16}$/$C_{18}$), palmitoleyl alcohol ($C_{16}$), heptadecyl alcohol ($C_{17}$), stearyl alcohol ($C_{18}$), nonadecyl alcohol ($C_{19}$), arachidyl alcohol ($C_{20}$), heneicosyl alcohol ($C_{21}$), behenyl alcohol ($C_{22}$), erucyl alcohol ($C_{22}$), lignoceryl alcohol ($C_{24}$), ceryl alcohol ($C_{26}$), 1-heptacosanol ($C_{27}$), montanyl alcohol ($C_{28}$), 1-nonacosanol ($C_{29}$), myricyl alcohol ($C_{30}$), lacceryl alcohol ($C_{32}$), geddyl alcohol ($C_{34}$) and tetratriacontanol ($C_{36}$), and mixtures thereof.

Exemplary fatty alcohols include, but are not limited to, decyl alcohol, lauryl alcohol, tridecyl alcohol, myristyl alcohol, pentadecyl alcohol, cetyl alcohol, isocetyl alcohol, cetearyl alcohol, palmitoleyl alcohol, heptadecyl alcohol, stearyl alcohol, isostearyl alcohol, oleyl alcohol, nonadecyl alcohol, arachidyl alcohol, heneicosyl alcohol, behenyl alcohol, erucyl alcohol, lignoceryl alcohol, ceryl alcohol, 1-heptacosanol, montanyl alcohol, 1-nonacosanol, myricyl alcohol, lacceryl alcohol, geddyl alcohol, tetratriacontanol, lanolin alcohol and palm alcohol, and mixtures thereof. In one embodiment, the fatty alcohol is behenyl alcohol cetyl alcohol, stearyl alcohol or mixtures thereof. In one embodiment, the fatty alcohol is behenyl alcohol.

In one embodiment, the fatty alcohols include, but are not limited to, behenyl alcohol, isostearyl alcohol, caprylyl alcohol, decyl alcohol, lauryl alcohol, myristyl alcohol, lanolin alcohol, lignoceryl alcohol, arachidyl alcohol, oleyl alcohol, palm alcohol, isocetyl alcohol, cetyl alcohol, stearyl alcohol and cetearyl alcohol, and mixtures thereof.

In an embodiment, the straight chain fatty alcohol is cetyl alcohol ($C_{18}$).

In one embodiment, the straight chain fatty alcohol is behenyl alcohol ($C_{22}$).

In another embodiment, the straight chain fatty alcohol is a mixture of cetyl alcohol ($C_{16}$) and behenyl alcohol ($C_{22}$).

The fatty alcohol and the fatty acid may react to form an ester when both are present in the composition. In an embodiment, the ester, when formed, is a cetyl behenate and/or behenyl behenate.

In yet another embodiment, the at least one oil and/or fat is an ester. The ester may be from a branched or straight chain fatty acid and a branched or straight chain fatty alcohol ("the ester"). It is recognized that because there are two components to the ester, either one or both of them can be branched or straight chained components, e.g. the ester can be mixed. For example, the fatty acid component may be branched and the fatty alcohol may be straight chained. Alternatively, the fatty acid component may be straight chained and the fatty alcohol may be branched. In another embodiment, both the acid and the alcohol may be branched. In yet another embodiment both the acid and the alcohol may be straight chained.

In an embodiment, the ester comprises a mixture of compounds having mono- and poly-branching in the acid and alcohol originating parts of the ester. In one embodiment, the fatty acid and fatty alcohol are alkyl branched.

In an embodiment, when the composition comprises an ester of a branched or straight chain fatty acid and a branched or straight chain fatty alcohol, the composition may further comprise a fatty acid.

In an embodiment, the branched fatty acid component of the ester is a $C_{12}$ to $C_{36}$ branched fatty acid, a $C_{12}$ to $C_{30}$ branched fatty acid, a $C_{14}$ to $C_{26}$ branched fatty acid, a $C_{16}$ to $C_{22}$ branched fatty acid, or a $C_{18}$ branched fatty acid.

As noted above, fatty acids suitable for use in the ester can be obtained from natural sources or can also be synthetically prepared.

For example, the fatty acids may be obtained from palm oil, rape seed oil, palm kernel oil, coconut oil, babassu oil, soybean oil, castor oil, sunflower oil, olive oil, linseed oil, cottonseed oil, safflower oil, tallow, whale or fish oils, grease, lard and mixtures thereof. The fatty acids can also be synthetically prepared. Relatively pure unsaturated fatty acids such as oleic acid, linoleic acid, linolenic acid, palmitoleic acid, and elaidic acid may be isolated, or relatively crude unsaturated fatty acid mixtures may be used as a basis for chemical modification.

Fatty acids suitable for use in the ester can be obtained from natural sources or can also be synthetically prepared. For example, the fatty acids may be obtained from palm oil, rape seed oil, palm kernel oil, coconut oil, babassu oil, soybean oil, castor oil, sunflower oil, olive oil, linseed oil, cottonseed oil, safflower oil, tallow, whale or fish oils, grease, lard and mixtures thereof. Or they could have come from mixtures of wax esters that have been modified to be predominantly fatty acid mixtures (ester hydrolysis). The fatty acids can also be synthetically prepared. Relatively pure unsaturated fatty acids such as oleic acid, linoleic acid, linolenic acid, palmitoleic acid, and elaidic acid may be isolated, or relatively crude unsaturated fatty acid mixtures may be used as a basis for chemical modification.

Exemplary branched fatty acids for use in the ester include, but are not limited to, iso-acids such as isostearic acid, isopalmitic acid, isomyristic acid, isoarachidic acid and isobehenic acid, neo-acids such as neodecanioc acid, and/or anti-iso acids. In one embodiment, the branched fatty acid for use in the ester is isostearic acid.

In an embodiment, the branched fatty alcohol component of the ester is a $C_{12}$ to $C_{36}$ branched fatty alcohol, a $C_{12}$ to $C_{30}$ branched fatty alcohol, a $C_{14}$ to $C_{26}$ branched fatty alcohol, a $C_{16}$ to $C_{22}$ branched fatty alcohol, or a $C_{18}$ branched fatty alcohol.

In another embodiment, the ester is an ester of a $C_{16}$ to $C_{22}$ branched fatty acid and a $C_{16}$ to $C_{22}$ branched fatty alcohol. The branched fatty acid and branched fatty alcohol may comprise the same number of carbon atoms, or a different number of carbon atoms. In one embodiment, the branched fatty acid and branched fatty alcohol comprise the same number of carbon atoms.

The ester may comprise one or more variations selected from the group comprising mono-branched fatty acid and poly-branched fatty alcohol, mono-branched fatty acid and mono-branched fatty alcohol, poly-branched fatty acid and mono-branched fatty alcohol, and poly-branched fatty acid and poly-branched fatty alcohol. The ester may be selected from this group by any suitable separation method. For example, the selected ester may be selected from a mixture of esters using a clathration method.

Exemplary branched fatty alcohols for use in the ester include, but are not limited to iso-alcohols such as isostearyl alcohol, isotetradecanol, isocetyl alcohol, isoarachidyl alcohol, isobehenyl alcohol and isolignoceryl alcohol; neo-alcohols such as neocapric alcohol; and/or anti-iso alcohols. In one embodiment, the fatty alcohol for use in the ester is isostearyl alcohol.

Exemplary esters generally can include, but are not limited to, coco-caprylate/caprate, diethyl sebacate, diisopropyl adipate, diisopropyl dilinoleate, ethyl oleate, ethylhexyl hydroxystearate, glycol distearate, glycol stearate, hydroxyoctacosanyl hydroxystearate, isopropyl isostearate, isostearyl isostearate, isopropyl myristate, isopropyl palmitate, isopropyl stearate, methyl glucose sesquistearate, methyl laurate, methyl salicylate, methyl stearate, myristyl lactate, octyl salicylate, oleyl oleate, PPG-20 methyl glucose ether distearate, propylene glycol diacetate, propylene glycol dicaprylate, propylene glycol monolaurate, propylene glycol monopalmitostearate, propylene glycol ricinoleate and sucrose distearate, and mixtures thereof.

In an embodiment, the ester is an ester of a $C_{16}$ to $C_{30}$ branched fatty acid and a $C_{16}$ to $C_{30}$ branched fatty alcohol.

In one embodiment, the ester comprises a C18 mono- and/or poly-branched fatty acid and a C18 mono- and/or poly-branched fatty alcohol.

In an embodiment, the ester is isostearyl isostearate ("ISIS").

In another embodiment, the ester is an ester of a $C_{16}$ to $C_{30}$ straight chain fatty acid and a $C_{16}$ to $C_{30}$ straight chain fatty alcohol.

In an embodiment, the ester is heptadecanoyl heptadecanoate ("HDHD").

In a further embodiment, the at least one oil and/or fat is an ester of glycerine (including mono-, di- and tri-esters). Exemplary esters of glycerin include, but are not limited to, caprylic/capric triglycerides, caprylic/capric/succinic triglyceride, cocoglycerides, glyceryl citrate, glyceryl isostearate, glyceryl laurate, glyceryl monostearate, glyceryl oleate, glyceryl palmitate, glyceryl ricinoleate, glyceryl stearate, mono and diglyceride, PEG-12 glyceryl laurate, PEG-120 glyceryl stearate, polyglyceryl-3 oleate, polyoxyl glyceryl stearate, tallow glycerides and medium chain triglycerides, and mixtures thereof. In one embodiment, triglycerides isolated from palm oil are preferred. In one embodiment, the ester of glycerin is caprylic/capric triglyceride.

In yet a further embodiment, the at least one oil and/or fat is a wax. Exemplary waxes include, but are not limited to, animal waxes, plant waxes, mineral waxes, silicone waxes, synthetic waxes and petroleum waxes. Suitable waxes include, but are not limited to, rice bran wax, carnauba wax, paraffin wax, white wax, candelilla wax, beeswax, jojoba wax, ozokerite and a spingolipid or a spingolipid mimic such as a ceramide, and mixtures thereof. In one embodiment the waxes are rice bran wax, carnauba wax, paraffin wax, white wax, candelilla wax, beeswax, jojoba wax and ozokerite, and mixtures thereof.

In one embodiment there is the optional inclusion of a sphingolipid or a sphingolipid mimic. Ceramides, acylceramides and glucosylceramides are all members of the "sphingoid" or "spingolipids" class. As noted above, these are compounds which have a backbone of sphingosine or a closely related structure to which either fatty acids or co-esterified fatty acids are linked through an amide linkage at the amino group of the sphingosine structure and in the case of a glucosylceramide, those to which saccharide moieties are linked to the terminal hydroxyl of the sphingosine structure through a glycosidic bond.

More specifically, ceramides are a family of waxy lipid molecules composed of sphingosine and a fatty acid. They contain an acyl linkage, and chain length most abundant in healthy skin is $C_{24}$-$C_{26}$ with a small fraction having an acyl chain length of $C_{16}$-$C_{18}$. Ceramides are found extensively in the stratum corneum. Ceramides are commercially available from major chemical suppliers such as Evonik, Mobile, Ala., USA or Sigma Chemical Company, St. Louis, Mo., U.S.A. In one embodiment the sphingolipid is other than a ceramide.

Exemplary ceramides useful in the present compositions include, but are not limited to, ceramide-1, -2, -3, -4, -5, -6 or -7, and mixtures thereof. Other ceramides known to those of skill in the art as useful in topical compositions are further contemplated as useful in the present compositions, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide", U.S. Food and Drug Administration (FDA) Center for Drug Evaluation and Research (CDER) Office of Management, January 1996, the contents of which are hereby incorporated by reference in their entirety. In one embodiment, the ceramide is ceramide-3. Suitably, the ceramide if present is in the lamellar membrane structure in an amount from about 0.001% to about 1% by weight, based on the total weight of the composition.

In one embodiment, the sphingoid or sphingolipid is a ceramide or a phytospingosine. In one embodiment, the sphingoid or sphingolipid is a phytospingosine.

In an embodiment, the at least one oil and/or fat is a sterol. Exemplary sterols include, but are not limited to, *Brassica Campestris* sterols, $C_{10}$-$C_{30}$ cholesterol/lanosterol esters, canola sterols, cholesterol, cholesterols, glycine soja sterols, PEG-20 phytosterol and phytosterols, and mixtures thereof.

Phytosterols are natural components of common vegetable oils. Exemplary sources of phytosterols useful in this regard include, but are not limited to, shea butter, vegetable oil, tall oil, sesame oil, sunflower oil, sunflower seed oil, rice bran oil, cranberry seed oil, pumpkin seed oil and avocado wax, and mixtures thereof. In one embodiment, the source of phytosterols is shea butter.

Phytosterols are typically incorporated in the basal membrane of the skin and can pass to the skin's surface through the differentiation of skin cells. Accordingly, phytosterols provide an improved caring and protecting effect. The topical application of phytosterols also usually leads to an increased skin moisture level and to increased lipid content. This improves the desquamation behavior of the skin and reduces erythemas which may be present. R. Wachter, Parf. Kosm., Vol. 75, p. 755 (1994) and R. Wachter, Cosm. Toil., Vol. 110, p. 72 (1995), each of which are incorporated herein by reference in their entirety, further demonstrate these advantageous properties of phytosterols.

Suitably, the phytosterol, source of phytosterols, cholesterol, or cholesterol derivative is present in the at least one lamellar membrane structure in an amount from about 0.05% to about 2% by weight, based on the total weight of the composition.

One embodiment of the composition is the inclusion of a phytosterol, cholesterol or cholesterol derivative in combination with a sphingoid or sphingolipid. More preferably, the sphingoid or sphingolipid is a ceramide and/or is a phytospingosine.

In another embodiment, the at least one oil and/or fat is a hydrocarbon. Exemplary hydrocarbons include, but are not limited to, dodecane, petrolatum, mineral oil, squalane, squalene and paraffin, and mixtures thereof. In one embodiment, the hydrocarbon is petrolatum, or a mixture of petrolatum and another oil or fat. In another embodiment, the hydrocarbon is a mixture of petrolatum and a second hydrocarbon. In another embodiment, the hydrocarbon is a mixture of mineral oil and a second hydrocarbon. In yet another embodiment, the hydrocarbon is a mixture of petrolatum and squalane. In yet another embodiment, the hydrocarbon is a mixture of mineral oil and squalane. In yet another embodiment, the hydrocarbon is a mixture of petrolatum and mineral oil.

Squalane helps enhance the skin's natural barrier function, protect the skin against the elements, and boost the skin's ability to retain moisture. Squalane is a component of human stratum corneum. Squalane is available in purified form (see e.g. Fitoderm® available from BASF) and may be used in the compositions in its purified form. Alternatively, an oil which is rich in squalane may be used.

Exemplary sources of squalane useful in the present compositions include, but are not limited to, shark liver oil, olive oil, palm oil, wheat germ oil, amaranth oil, rice bran oil and sugar cane. It is understood that squalane from these sources of oils is considered a lipid component. In one embodiment, squalane isolated from olive oil is preferred. Suitably, the squalane is present in the at least one lamellar membrane structure in an amount from about 0.05% to about 2% by weight, based on the total weight of the composition.

In yet another embodiment, the at least one oil and/or fat is an essential oil. Exemplary essential oils include, but are not limited to, primrose oil, rose oil, *eucalyptus* oil, borage oil, bergamot oil, chamomile oil, citronella oil, lavender oil, peppermint oil, pine oil, pine needle oil, spearmint oil, tea tree oil and wintergreen oil, and mixtures thereof.

In a further embodiment, the at least one oil and/or fat is a vegetable oil. Exemplary vegetable oils include, but are not limited to, olus (vegetable) oil, almond oil, aniseed oil, canola oil, castor oil, coconut oil, corn oil, avocado oil, cottonseed oil, olive oil, palm kernel oil, peanut oil, sunflower oil, safflower oil and soybean oil, including hydrogenated and non-hydrogenated versions thereof, and mixtures thereof.

In yet a further embodiment, the at least one oil and/or fat is an edible oil. Exemplary edible oils include, but are not limited to, cinnamon oil, clove oil, lemon oil and peppermint oil, and mixtures thereof.

In an embodiment the oil is a fatty acid, a source of fatty acids, or an ester of glycerin as described herein. In an embodiment, the source of fatty acids is olus (vegetable) oil, olive oil or rice bran oil.

Suitably, the discontinuous oil phase is present in an amount from about 5% to about 70% by weight, based on the total weight of the composition. In one embodiment, the discontinuous oil phase is present in an amount from about 20% to about 70% by weight, based on the total weight of the composition. In another embodiment, the discontinuous oil phase is present in an amount from about 5% to about 50% by weight, based on the total weight of the composition. In another embodiment, the discontinuous oil phase is present in an amount from about 5% to about 45% by weight, based on the total weight of the composition. In yet another embodiment, the discontinuous oil phase is present in an amount from about 5% to about 35% by weight, based on the total weight of the composition.

Aqueous Phase

The compositions comprise a continuous aqueous phase. The aqueous phase comprises water. Suitably, any additional components such as glycerin and any other water soluble excipients will be dissolved in this aqueous phase.

Suitably, the continuous aqueous phase is present in an amount from about 10% to about 90% by weight, based on the total weight of the composition. In an embodiment, the continuous aqueous phase is present in an amount from about 25% to about 90% by weight, based on the total weight of the composition. In another embodiment, the continuous aqueous phase is present in an amount from about 45% to about 90% by weight, based on the total weight of the composition. In another embodiment, the continuous aqueous phase is present in an amount from about 25% to about 75% by weight, based on the total weight of the composition. In another embodiment, the continuous aqueous phase is present in an amount from about 10% to about 70% by weight, based on the total weight of the composition. In a further embodiment, the continuous aqueous phase is present in an amount from about 60% to about 90% by weight, based on the total weight of the composition.

In an embodiment, the continuous aqueous phase comprises water in an amount from about 13% to about 60% by weight, in another embodiment from about 20% to about 40% by weight, and in another embodiment from about 10% to about 35% by weight, based on the total weight of the composition.

In an embodiment, the continuous aqueous phase comprises glycerin in an amount from about 1% to about 40% by weight, based on the total weight of the composition. In another embodiment, the continuous aqueous phase comprises glycerin in an amount from about 5% to about 15% by weight, based on the total weight of the composition. In yet another embodiment, the continuous aqueous phase comprises glycerin in an amount of about 10% by weight, based on the total weight of the composition.

In one embodiment, the continuous aqueous phase may also include a sugar alcohol, such as glucose, glycerol, sorbitol, mannitol, maltitol, galactitol, erythritol, xylitol, inositol, lactitol, and mixtures thereof. In one embodiment, the sugar alcohol is glucose. The sugar alcohol may be present in an amount from about 1% to about 20% by weight, based on the total weight of the composition.

The continuous aqueous phase may further comprise other water miscible components, such as for example, humectants and pH adjusting agents.

Thickening Agent

The compositions of the invention comprise at least one thickening agent or rheology modifier. In an embodiment, the thickening agent is a mixture of two or more thickening agents.

The function of the thickening agent is to stabilize the discontinuous oil phase of the composition. The thickening agent may also provide hardness and structural support useful in forming a stick composition, for example. Thickening agents may be water miscible which are used to thicken the aqueous portion of the emulsion composition. Other thickening agents are nonaqueous making them suitable for thickening the oil phase of the emulsion composition. Yet other thickening agents such as those described below, may act at the oil-water interface and thus lie at the interphase boundary.

Exemplary water miscible thickening agents include, but are not limited to, a cellulose derivative such as carboxymethylcellulose, hydroxyethylcellulose, hydroxypropylcellulose, hydroxypropyl methylcellulose; agar; carrageenan; curdlan; gelatin; gellan; β-glucan; tragacanth gum; guar gum; gum arabic; locust bean gum; pectin; starch; a carbomer, such as sodium carbomer; a xanthan derivative such as dehydroxanthan gum and xanthan gum; salts thereof, or a combination or mixture thereof. In one embodiment, the thickening agent is a carbomer or a salt thereof, such as sodium carbomer. In a further embodiment, the thickening agent is hydroxyethylcellulose.

Exemplary nonaqueous thickening agents include, but are not limited to, acrylate copolymers, VP/Eicosene copolymer, waxes, fatty alcohols and fatty acids, as described herein.

In one embodiment, the thickening agent is a fatty alcohol. Suitable fatty alcohols include, but are not limited to, behenyl alcohol, isostearyl alcohol, caprylyl alcohol, decyl alcohol, lauryl alcohol, myristyl alcohol, lanolin alcohol, arachidyl alcohol, oleyl alcohol, palm alcohol, isocetyl alcohol, cetyl alcohol, stearyl alcohol and cetearyl alcohol, and mixtures thereof.

Other suitable fatty alcohols include, but are not limited to, tridecyl alcohol, pentadecyl alcohol, isocetyl alcohol, palmitoleyl alcohol, heptadecyl alcohol, isostearyl alcohol, oleyl alcohol, nonadecyl alcohol, heneicosyl alcohol, behenyl alcohol, erucyl alcohol, lignoceryl alcohol, ceryl alcohol, 1-heptacosanol, montanyl alcohol, 1-nonacosanol, myricyl alcohol, lacceryl alcohol, geddyl alcohol, tetratriacontanol, and lanolin alcohol, and mixtures thereof.

In one embodiment, the thickening agent is a fatty acid which may be saturated or unsaturated, branched or straight chained), or a source of fatty acids, and mixtures thereof.

Suitable fatty acids include, but are not limited to, isostearic acid, linoleic acid, linolenic acid, oleic acid, myristic acid, ricinoleic acid, columbinic acid, arachidic acid, arachidonic acid, lignoceric acid, nervonic acid, eicosapentanoic acid, palmitic acid, stearic acid and behenic acid, and mixtures thereof.

Other exemplary fatty acids include, but are not limited to lauric acid, tridecylic acid, myristic acid, pentadecylic acid, margaric acid, oleic acid, nonadecylic acid, arachidic acid, arachidonic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid and hexatriacontylic acid, and mixtures thereof.

In one embodiment, the thickening agent comprises a mixture of fatty alcohols, a cellulose derivative, a xanthan derivative, a non-aqueous agent, and a carbomer. In one embodiment, the thickening agent comprises behenyl alcohol, dehydroxanthan gum, VP/Eicosene copolymer, acrylates/C10-30 alkyl acrylate cross polymer and sodium carbomer. In an embodiment, the thickening agent is a mixture of polyacrylate crosspolymer-6 and hydroxyethyl acrylate/sodium acryloyldimethyl taurate copolymer.

In an embodiment, the thickening agent is an acrylate copolymer, such as acrylates/C10-30 alkyl acrylate cross polymer, polyacrylate crosspolymer-6, or a mixture of hydroxyethyl acrylate and sodium acryloyldimethyl taurate copolymer.

In one embodiment, the thickening agent is polyacrylate crosspolymer-6. Polyacrylate crosspolymer-6 is available as "Sepimax Zen" from Seppic, a subsidiary of Air Liquide Group.

In another embodiment, the thickening agent is a mixture of hydroxyethyl acrylate and sodium acryloyldimethyl taurate copolymer. A mixture of hydroxyethyl acrylate and sodium acryloyldimethyl taurate copolymer is available as "Sepinov Weo" from Seppic, a subsidiary of Air Liquide Group.

In yet another embodiment, the thickening agent is a mixture of polyacrylate crosspolymer-6 and hydroxyethyl acrylate/sodium acryloyldimethyl taurate copolymer.

In one embodiment, the thickening agent is xanthan gum. In another embodiment, the thickening agent is dehydroxanthan gum. In yet another embodiment, the thickening agent is a carbomer or a salt thereof, such as sodium carbomer. In a further embodiment, the thickening agent is hydroxyethylcellulose.

Suitably, the thickening agent is present in an amount from about 0.1% to about 10% by weight, based on the total weight of the composition. In an embodiment, the thickening agent is present in an amount from about 0.2% to about 5% by weight, based on the total weight of the composition. In an embodiment, the thickening agent is present in an amount from about 1% to about 5% by weight, based on the total weight of the composition. In another embodiment, the thickening agent is present in an amount from about 0.2% to about 2% by weight, based on the total weight of the composition.

Lamellar Membrane Structure

The compositions of the invention comprise at least one lamellar membrane structure. Generally this refers to a planar lipid bilayer sheet, or a slight curve around a droplet of oil. They may also exist as separate discrete lamellae in the bulk aqueous phase. This is in contrast to a rounded formed liposomal structure. In another embodiment, the respective lamellar membrane structures form two or more stacked lamellar membrane structures, sometimes referenced as a liquid crystal. Two lamellar membrane structures stacked together, one on top of the other, is known as a double lamellar membrane structure.

In an O/W emulsion the surfactant-emulsifiers orientate so that the hydrophilic heads face out into the continuous phase and the hydrophobic tails are anchored within the oil droplet. In the case of a liposome, these are typically aqueous filled cores where the hydrophilic heads of the interfacial layer of surfactant-emulsifer (here shown as a dialkyl phospholipid which can form liposomal structures) orientated toward the hydrophilic aqueous core and for the outermost layer, orientated towards the continuous phase.

Even if systems contain lamellar forming ingredients such as those further described herein, those systems can be prepared in a manner that will yield either a liposome or O/W emulsion. The physical characteristics of each system is different and is outlined below.

The properties described above are measurable using standard lab measurement methods available in the art. All of these properties will clearly provide for an accurate designation of those O/W emulsions (microscopy, rheology, visual assessment) having lamellar structures (e.g. with FTIR/XRD).

In an embodiment, at least one lamellar membrane structure comprises a phospholipid and and (ii) a fatty alcohol as herein defined.

In an embodiment, the at least one lamellar membrane structure further comprises a fatty acid.

In an embodiment, at least one lamellar membrane structure comprises a phospholipid, (ii) a fatty alcohol, and (iii) a fatty acid.

In an embodiment, at least one lamellar membrane structure comprises a phospholipid, (ii) a fatty alcohol, (iii) a fatty acid, and (iv) a fatty ester. In another embodiment, the fatty ester is comprised of a branched or straight chain fatty acid and a branched or straight chain fatty alcohol.

In one embodiment, the at least one lamellar membrane structure comprises (i) a phospholipid, (ii) a fatty alcohol, (iii) a fatty acid, and (iv) an ester of a branched fatty acid and a branched fatty alcohol.

In another embodiment, the at least one lamellar membrane structure comprises (i) a phospholipid, (ii) a fatty alcohol, (iii) a fatty acid, and (iv) an ester of a straight chain fatty acid and a straight chain fatty alcohol.

In another embodiment, the at least one lamellar membrane structure comprises (i) a phospholipid, (ii) a fatty alcohol, (iii) a fatty acid, and (iv) an ester of a mixture of straight or branched chain fatty acids and fatty alcohols.

In one embodiment the lamellar blend contains a fatty alcohol of C16-18 chain length (branched or straight chain), and a second longer (branched or straight chain) fatty alcohol of a C22-C30 carbon atoms.

Suitably, the components of the lamellar membrane structure are present in an amount from about 2.5% to about 20% by weight, based on the total weight of the composition. In an embodiment, the components of the lamellar membrane structure are present in an amount from about 3% to about 15% by weight, based on the total weight of the composition. In another embodiment, the components of the lamellar membrane structure are present in an amount of about 3%, 4%, 5%, 6%, 7%, 8%, 9%, 10%, 11%, 12%, 13%, 14% or 15% by weight, based on the total weight of the composition. In one embodiment, the components of the lamellar membrane structure are present in an amount of about 8.8% by weight, based on the total weight of the composition.

| Property | O/W Emulsion | Aqueous Core Liposome |
|---|---|---|
| Droplet size | Typically >1000 nm | Range from 25 nm to 500 nm |
| Opacity | Very often white in appearance due to greater interaction with visible light. | Can be translucent to blue due to wavelength of light absorption/reflection |
| Rheology/Viscosity | Mid to high viscosity system (attributable to long range interactions between droplets) | Tend towards low viscosity systems (limited long range interactions between systems) |
| Dynamic Lamellar Structure (Viscosity Building) | Viscosity can build post manufacture due to thermodynamic equilibration. Lamellar structure builds with time causing an increase in viscosity. | Viscosity is relatively stable as lamellar structure has been established during the manufacturing process. |

Suitably, the ester is present in the lamellar membrane blend in an amount from about 0.1% to about 75% by weight. In an embodiment, the ester is present in an amount of about 1% to about 50% by weight. In another embodiment, the ester is present from about 5% to about 50% by weight. In another embodiment, the ester is present from about 5% to about 35% by weight based on the total weight of the lamellar membrane blend. In one embodiment, the ester is present in the lamellar membrane blend in an amount from about 1% to about 25% by weight, based on the total weight of the lamellar membrane blend. In one embodiment the ester is present in an amount from about 0.1% to about 5% by weight, based on the total weight of the composition. In another embodiment the ester is present in an amount from about 1% to about 5% by weight, based on the total weight of the composition.

Suitably, the fatty acid is present in the lamellar blend in an amount from about 0.1% to about 5% by weight, based on the total weight of the composition. In another embodiment, the fatty acid is present in the lamellar blend in an amount from about 0.25% to about 2.5% by weight, or from about 0.5% to about 2.5% by weight, based on the total weight of the composition.

In one embodiment, the fatty alcohol is present in in the lamellar blend in an amount from about 2% to about 15% by weight, based on the total weight of the composition. In another embodiment, the fatty alcohol is present in in the lamellar blend in an amount from about 2% to about 10% by weight, or from about 2% to about 7.5% by weight, based on the total weight of the composition.

In another embodiment, the at least one lamellar membrane structure comprises a (i) a phospholipid, (ii) a fatty alcohol, (iii) a fatty acid, (iv) an ester of a branched fatty acid and a branched fatty alcohol and squalane.

In another embodiment, the at least one lamellar membrane structure comprises a (i) a phospholipid, (ii) a fatty alcohol, (iii) a fatty acid, (iv) an ester of a branched fatty acid and a branched fatty alcohol and at least one of rice bran oil and/or rice bran wax.

In another embodiment, the at least one lamellar membrane structure comprises a (i) a phospholipid, (ii) a fatty alcohol, (iii) a fatty acid, (iv) an ester of a branched fatty acid and a branched fatty alcohol, and at least one of a phytosterol, squalane, rice bran oil and/or rice bran wax. In yet a further embodiment, the at least one lamellar membrane structure further comprises a ceramide.

In another embodiment, the at least one lamellar membrane structure comprises a (i) a phospholipid, (ii) a fatty alcohol, (iii) a fatty acid, (iv) an ester of a branched fatty acid and a branched fatty alcohol at least one of a phytosterol, squalane, rice bran oil, rice bran wax, and a sphingolipid or a sphingolipid mimic. In one embodiment, the sphingolipid is other than a ceramide.

In another embodiment, the at least one lamellar membrane structure comprises a (i) a phospholipid, (ii) a fatty alcohol, (iii) a fatty acid, (iv) an ester of a branched fatty acid and a branched fatty alcohol, a phytosterol, and optionally at least one of squalane, rice bran oil, rice bran wax, pentylene glycol, and a sphingolipid or a sphingolipid mimic. In one embodiment, the sphingolipid is other than a ceramide.

In another embodiment, the at least one lamellar membrane structure comprises a (i) a phospholipid, (ii) a fatty alcohol, (iii) a fatty acid, (iv) an ester of a branched fatty acid and a branched fatty alcohol, and at least one of rice bran oil, rice bran wax, squalane, a phytosterol, cholesterol or cholesterol derivative, a sphingolipid or a sphingolipid mimic, or a triglyceride. In one embodiment, the sphingolipid is other than a ceramide.

Many of the lipids used in the present compositions are the same or similar to the lipids found in human stratum corneum.

Suitably, at least one lamellar membrane structurant is present in an amount from about 0.15 to about 5% by weight, based on the total weight of the composition.

The lamellar membrane structure can be prepared prior to formulating final compositions of the present invention. In one embodiment, the lamellar membrane structure may also be referred to as a dermal membrane structure, e.g. a DMS® concentrate (also referred to herein as Probiol™) prepared in accordance with the teachings of several patents and patent application as disclosed in detail in Albrecht et al., U.S. Pat. No. 7,001,604; Albrecht et al., US 2011/0027327; and Albrecht et al., WO 2007/112712 which disclosures are incorporated by reference in part.

In an embodiment, the phospholipid in the DMS® concentrate is hydrogenated lecithin, and the concentrate further comprises water and a lipid. In another embodiment, the lamellar membrane structure composition comprises a phospholipid, water, and rice bran oil and rice bran wax.

Rice bran oil is also known as *Oryza Sativa* bran oil, and rice bran wax is also known as *Oryza Sativa* Cera. Rice bran oil has a composition similar to peanut oil, with 38% monounsaturated, 37% polyunsaturated and 25% saturated fatty acids. Rice Bran Wax is the vegetable wax extracted from the bran oil of rice. It contains $C_{16}$-$C_{30}$ fatty acids in the form of wax esters.

In one embodiment, the lamellar membrane structure composition comprises hydrogenated lecithin, shea butter, squalane, pentylene glycol, glycerin, palmitioyl monoethanolamide (MEA) or referred to as (PMEA), water, and optionally ceramide-3, rice bran oil, rice bran wax, orphytosphingosine.

Kuhs GmBH has provided commercial information on various lamellar concentrates under the DMS® Concentrate line as DMS® 03007, 03015, 03016, 03017, 03020 and 03031 which are included for use within the invention herein.

TABLE 1

| Probiol No. | Lipids | Preservative | Colour | INCI |
|---|---|---|---|---|
| N 03007 | Caprylic/Capric Triglycerides Hydrogenated Lecithin | Alcohol | White | Aqua & Alcohol & Caprylic/Capric Triglycerides & Hydrogenated Lecithin |
| N 03015 | Caprylic/Capric Triglycerides Shea Butter Squalane Ceramide 3 Hydrogenated Lecithin | Alcohol | White | Aqua & Alcohol & Caprylic/Capric Triglycerides & Hydrogenated Lecithin & Butyrospermum Parkii & Squalane & Ceramide 3 |

TABLE 1-continued

| Probiol No. | Lipids | Preservative | Colour | INCI |
|---|---|---|---|---|
| N 03017 | Caprylic/Capric Triglycerides Shea Butter Squalane Ceramide 3 Hydrogenated Lecithin | Alcohol Propylene Glycol | White | Aqua & Alcohol & Caprylic/Capric Triglycerides & Hydrogenated Lecithin & Propylene Glycol & Butyrospermum Parkii & Squalane & Ceramide 3 |
| N 03020 | Caprylic/Capric Triglycerides Hydrogenated Lecithin | Alcohol Propylene Glycol | White | Aqua & Alcohol & Caprylic/Capric Triglycerides & Hydrogenated Lecithin & Propylene Glycol |
| N 03031 | Caprylic/Capric Triglycerides Shea Butter Squalane Ceramide 3 Hydrogenated Lecithin | Pentylene Glycol | White | Aqua & Hydrogenated Lecithin & Caprylic/Capric Triglycerides & Pentylene Glycol & Butyrospermum Parkii & Glycerin & Squalane & Ceramide 3 |

Suitably, the lamellar membrane structure as a concentrate can represent a phase in the final composition of about 1% to about 90% by weight, based on the total weight of the final composition. In one embodiment, the concentrate is present in an amount from about 10% to about 50% by weight, based on the total weight of the composition. In another embodiment, the lamellar membrane structure as a concentrate is present in an amount from about 10% to about 30% by weight, based on the total weight of the composition. In yet another embodiment, the lamellar membrane structure as a concentrate is present in an amount of about 15% by weight, based on the total weight of the composition.

In another embodiment of the disclosure, the lamellar membrane structure may further comprise at least one alcohol, in particular a polyvalent alcohol. Suitable polyvalent alcohols include, but are not limited to, pentylene glycol, caprylyl glycol, phenylethyl alcohol, decylene glycol, glycerin or mixtures thereof. In one embodiment, the lamellar membrane structure comprises glycerin. In another embodiment, the lamellar membrane structure comprises pentylene glycol. In another embodiment, the lamellar membrane structure comprises pentylene glycol and glycerin.

Dermatologically Acceptable Excipients

The compositions of the invention may further comprise at least one dermatologically acceptable excipient.

In an embodiment, the dermatologically acceptable excipient is selected from the group consisting of an antioxidant, a chelating agent, a preservative, a colorant, a sensate, a moisturizer, a humectant, a lip conditioning agent and a pH adjusting agent, and mixtures thereof.

In an embodiment, the compositions of the invention are free or substantially free of a conventional emulsifier.

Antioxidant

The compositions of the invention may further comprise an antioxidant. In an embodiment, the antioxidant is a mixture of two or more antioxidants.

Antioxidants may protect the composition from oxidation (e.g. becoming rancid) and/or provide lip conditioning benefits upon application to the lips. Tocopherol, tocopheryl acetate, some botanical butters, niacinamide, pterostilbene (trans-3,5-dimethoxy-4-hydroxystilbene) magnolol, and green tea extracts, alone or in combination thereof are exemplary natural product antioxidants suitable for use in the compositions. Other suitable antioxidants include ascorbic acid and esters thereof such as ascorbyl palmitate, butylated hydroxytoluene (BHT), butylated hydroxyanisole (BHA), propyl gallate, vitamin E TPGS, ethyl ferulate, ferulic acid, resveratrol, 2,2-dimethyl chroman (Lipochroman®), singapine, tetrahydrocurcumin or other curcumin derivatives, hydroxytyrosol, Bis-Ethylhexyl Hydroxydimethoxy Benzylnalonate (Ronacare AP®), dimethylmethoxy chromanyl palmitate (Chromabright®) or a combination or mixture thereof. It is recognized that a combination or mixture of all of these antioxidants is also suitable for use herein. In one embodiment, the antioxidant is tocopherol, or a mixture of tocopherol and ascorbyl palmitate. In another embodiment, the antioxidant is niacinamide.

Suitably, the antioxidant is present in an amount from about 0.001% to about 1% by weight, based on the total weight of the composition.

Chelating Agents

The compositions of the invention may further comprise a chelating agent. In an embodiment, the chelating agent is a mixture of two or more chelating agents.

Exemplary chelating agents include, but are not limited to, citric acid, glucuronic acid, sodium hexametaphosphate, zinc hexametaphosphate, ethylenediamine tetraacetic acid (EDTA), ethylenediamine disuccinic acid (EDDS), phosphorates, salts thereof, or a combination or mixture thereof.

In one embodiment, the chelating agent is EDTA or a salt thereof, such as potassium, sodium or calcium salts of EDTA. In another embodiment, the chelating agent is ethylenediamine succinic acid or a salt thereof, such as potassium, sodium or calcium salts. In one particular embodiment, the chelating agent is trisodium ethylenediamine disuccinate.

Suitably, the chelating agent is present in an amount from about 0.1% to about 1% by weight, based on the total weight of the composition.

Preservative

The compositions of the invention may further comprise a preservative. In an embodiment, the preservative is a mixture of two or more preservatives.

Exemplary preservatives include, but are not limited to, benzyl alcohol, diazolidinyl urea or other substituted ureas and hydantoin derivatives, methyl paraben, ethyl paraben, propyl paraben, butyl paraben, phenoxyethanol, sorbic acid, benzoic acid, propylene glycol, pentylene glycol, hexylene glycol, salts thereof, or a combination or mixture thereof.

In an embodiment, the preservative is a combination of non-conventional preservatives, such as capryloyl glycine, 1,2-hexanediol and other glycols. Other suitable glycols include, but are not limited to, caprylyl glycol and/or pentylene glycol. In one embodiment, the preservative is a mixture of pentylene glycol and hexylene glycol.

Suitably, these preservatives are present in an amount from about 0.01% to about 5% by weight, based on the total weight of the composition. In another embodiment, the preservative is present in an amount from about 0.01% to about 2% by weight.

In one embodiment, the capryloyl glycine is present in an amount from about 0.5% to about 2% by weight and the additional glycols can be added in amounts up to 5% by weight, based on the total weight of the composition. Suitably, the preservative is a combination of at least capryloyl glycine and caprylyl glycol in an amount from about 0.5% to about 2% by weight, based on the total weight of the composition.

In an alternative embodiment, the compositions of the invention are free of conventional preservatives.

Moisturizer

The compositions of the invention may further comprise a moisturizer. Exemplary moisturizers useful in the present compositions include, but are not limited to, propylene glycol, dipropylene glycol, butylene glycol, pentylene glycol, hexylene glycol, polyethylene glycol, glycerin, sodium pyrrolidone carboxylate, α-hydroxy acids, β-hydroxy acids, ethoxylated and propoxylated polyols, polysaccharides, panthenol, sorbitol, hyaluronic acid and salts thereof, such as sodium, potassium or calcium salts, and mixtures thereof.

Suitably, the moisturizer is present in an amount from about 0.5% to about 10% by weight, based on the total weight of the composition.

Humectant

The compositions of the invention may further comprise a humectant. Exemplary humectants useful in the present compositions include, but are not limited to, glycerin, betaine, sarcosine, panthenol, propylene glycol, butylene glycol, pentylene glycol, hexylene glycol, caprylyl glycol, sorbitol and glucose, and mixtures thereof.

In one embodiment, the humectant is a mixture of glycerin and panthenol.

Suitably, the humectant is present in an amount from about 1% to about 15% by weight, based on the total weight of the composition.

pH Adjusting Agent

The compositions of the invention may further comprise a pH adjusting agent. In one embodiment, the pH adjusting agent is a base. Suitable bases include amines, bicarbonates, carbonates, and hydroxides such as alkali or alkaline earth metal hydroxides, as well as transition metal hydroxides. In an embodiment, the base is sodium hydroxide or potassium hydroxide.

In another embodiment, the pH adjusting agent is an acid, an acid salt, or mixtures thereof. Suitably, the acid is selected from the group consisting of lactic acid, acetic acid, maleic acid, succinic acid, citric acid, benzoic acid, boric acid, sorbic acid, tartaric acid, edetic acid, phosphoric acid, nitric acid, ascorbic acid, dehydroacetic acid, malic acid, propionic acid, sulphuric acid and hydrochloric acid, or a combination or mixture thereof.

In yet another embodiment, the pH adjusting agent is a buffer. Suitably, the buffer is selected from the group consisting of citrate/citric acid, acetate/acetic acid, phosphate/phosphoric acid, propionate/propionic acid, lactate/lactic acid, carbonate/carbonic acid, ammonium/ammonia and edetate/edetic acid, or a combination or mixture thereof.

Colorant

The compositions of the invention may further comprise a colorant that imparts color to the composition and/or lips. For a lip balm, the colorant should not be of an amount, particle size, and/or matrix that permits transfer of colorant to the lips during application. For a lipstick, a colorant that transfers and imparts color to the lips should be used. Colorants include, for example, natural colorants such as plant extracts, natural minerals, carmine, synthesized and/or processed colorant materials such as iron oxides, synthetic dyes, organic compounds, lake colorants, and FDA certified colorants for use on the lips. The above list is not an exhaustive list of colorants and those of skill in the art may consider the use of other colorants. Formulations of colorants are commercially available. An example of a commercially available colorant contains caprylic/capric triglycerides (59.5%), titanium dioxide (39.6%), castor oil phosphate (0.5%) and triethoxycaprylylsilane (0.4%). The use of a colorant containing titanium dioxide can affect the stability of some sunscreens such as Avobenzone. It has been observed that colorants containing coated titanium dioxide can enhance the stability of Avobenzone. Optionally, in some embodiments, it may be desirable to include a color enhancer such as, for example, a pearlescent material.

Sensate

The compositions of the invention may further comprise a sensate. A sensate is a composition that initiates a sensory perception such as heating or cooling, for example, when contacted with the skin and/or lips. Exemplary sensates include, but are not limited to, mint extracts, cinnamon extract and capsaicin. Preferred sensates are derived from natural sources. However, synthetic sensates are within the scope of this invention. Sensates typically have high potency and accordingly may yield significant impact at low levels. Suitably, the sensate is present in an amount from about 0.05% to about 5% by weight, based on the total weight of the composition.

Pharmaceutically Active Agent

The compositions of the invention may further comprise a pharmaceutically acceptable active agent.

Exemplary pharmaceutically active agents include, but are not limited to, an anti-inflammatory agent, an antibacterial agent, an antiviral agent, an antifungal agent, an anti-parasitic agent, a nutritional agent, a sunscreen, a sunblock, and mixtures thereof. Suitably, the pharmaceutically active agent is present in an amount from about 0.001% to about 30% by weight, depending on the nature of the active agent, the condition being treated, and the composition.

In one embodiment, the pharmaceutically active agent is an anti-inflammatory agent. Exemplary anti-inflammatory agents are niacinamide and N-acylalkanolamines including, but not limited to, lactamide monoethanolamide (MEA), oleamide MEA, acetamide MEA (AMEA), palmitioyl MEA (PMEA), N-acetylphosphatidylethanolamine, N-acetylethanolamine, N-oleoylethanolamine, N-linolenoylethanolamine, N-acylethanolamine, and N-acyl-2-hydroxy-propylamine. In one embodiment, the N-acylalkanolamine is present in an amount from about 0.01% to about 2% by weight, based on the total weight of the composition.

In one embodiment, the N-acylalkanolamine is palmitidyl MEA (PMEA).

Suitably, the N-acylalkanolamine is present in an amount from about 0.01% to about 2% by weight, based on the total weight of the composition.

In another embodiment, the anti-inflammatory agent is niacinamide.

Suitably, the niacinamide is present in an amount from about 0.01% to about 5% by weight, based on the total weight of the composition.

In another embodiment, the pharmaceutically active agent is a sunscreen. Suitably, the sunscreen is a UVA and/or UVB sunscreen. Suitably, the sunscreen is a combination of a UVA sunscreen and a UVB sunscreen.

Efficacious protection from UVA and UVB radiation requires the use of significant amounts of sunscreen, and often a mixture of organic sunscreens, to achieve efficacious protection from both UVA and UVB radiation. UVB radiation, which is radiation in the wavelength range of 290 nm-320 nm, has traditionally been characterized as the radiation that causes sunburn. In addition, UVB radiation can decrease enzymatic and non-enzymatic antioxidants in the skin and impair the natural protective mechanisms in the skin, thereby contributing to DNA damage and potentially skin cancer. The dangers of UVA radiation, which is radiation in the wavelength range of 320 nm to 400 nm, have only recently been recognized. Chronic exposure to UVA radiation can cause damage to gene P53 DNA, possibly leading to cancer. Additionally, the longer UVA wavelengths allow for relatively deep penetration into the skin tissues causing damage to the elastic fibers and collagen which give skin its shape, thus causing wrinkling and eventually premature skin aging. Thus, protecting the skin from UVA and UVB radiation is important for skin health and overall health more generally.

For purposes herein wavelength range is as follows: UVA1: 340-400 nm, UVA2: 320-340 nm, and UVB: 290-. Suitable UVA1 and UVA2 filters include, but are not limited to, Avobenzone (Butyl methoxy dibenzoyl methane) (Parsol 1789, Eusolex 9020), Bisdisulizole disodium (Neo Heliopan AP), Diethylamino hydroxybenzoyl hexyl benzoate (Uvinul A Plus), Drometrizole trisiloxane (Mexoryl XL), Menthyl anthranilate (Meradimate), oxybenzone, sulisobenzene and dioxybenzone, and mixtures thereof.

UVB filters include, but are not limited to, Amiloxate, 4-Aminobenzoic acid (PABA), Cinoxate, Ethylhexyl triazone/octyltriazone (Uvinul T 150), Homosalate, 4-Methylbenzylidene camphor (Parsol 5000), Octyl methoxycinnamate (Octinoxate) (Parsol MCX), Octyl salicylate/ ethylhexyl salicylate (Octisalate), Padimate O (Escalol 507), Phenylbenzimidazole sulfonic acid (Ensulizole), Polysilicone-15 (Parsol SLX), Enzacamene, and Trolamine salicylate, and mixtures thereof.

UVA+UVB filters include, but are not limited to, Bemotrizinol (Tinosorb S), Benzophenones 1-12, Dioxybenzone, -Terephthalylidene dicamphor sulfonic acid (Ecamsule) (Mexoryl SX), Diethylhexyl butamido triazone/Iscotrizinol (Uvasorb HEB), Octocrylene, Oxybenzone (Eusolex 4360), Benzophenone-4(Sulisobenzone), Bisoctrizole (Tinosorb M), Heliolex (a combination of avobenzone and oxybenzone), Phenylbenzimiazole sulfonic acid (Ensulizole), Benzophenone-8, and mixtures thereof.

Other exemplary sunscreens useful in the present invention (with maximum suitable amounts of each sunscreen in % wt/wt) include, but are not limited to, amino benzoic acid (about 15%), Avobenzone (about 3%), cinoxate (about 3%), octyl methoxycinnamate (Octinoxate) (about 10%), homosalate (about 15%), meradimate (about 5%), octocrylene (about 10%), ethylhexyl salicylate (also known as octyl salicylate or octisalate) (about 5%), oxybenzone (about 6%), dioxybenzone (about 3%), Octyldimethyl PABA (Padimate O) (about 8%), p-amyldimethyl PABA (Padimate A) (about 3%), Phenylbenzimidazole sulfonic acid (ensulizole)(about 4%), sulisobenzene (about 10%), trolamine salicylate (about 12%), benzophenone (about 10%), benzylidine compounds, such as 4-methylbenzylidine camphor (Parsol 5000) (about 6%), butyl methoxydibenzoylmethane (about 5%), bis-ethylhexyloxyphenol methoxyphenyl triazine (Bemotrizinol or Tinosorb S) (about 10%), camphor benzalkonium methosulfate (about 6%), diethyl amino hydroxy benzoyl hexyl benzoate (Uvinul A plus) (about 10%), diethylhexyl butamido triazine (Uvasorb HEB) (about 10%), disodium phenyl dibenzylmidazole tetrasulfonate (Bisdisulizole disodium or NeoHeliopan AP) (about 10%), drometrizole trisiloxane (silatriazole or Mexoryl XL) (about 15%), ethylhexyl dimethyl para-amino benzoic acid (about 8%), ethylhexyl methoxycinnamate (about 10%), ethylhexyl Triazone (Uvinul T 150) (about 5%), isoamyl p-methoxycinnamate (about 10%), 4-methylbenzylidene camphor (about 10%), methylene bis-benzotriazolyl tetramethylbutylphenol (Bisoctrizole or Tinosorb M) (about 10%), PEG-25 paramainobenzoic acid (about 5%), phenylbenziamido methylbenzylidene camphor (about 6%), diisopropyl methyl cinnamate (about 10%), dimethoxyphenyl-[1-(3,4)-4,4-dimethyl]1,3 pentanedione (about 7%), ethylhexyl dimethyloxy benzylidene dioxoimidazoline propionate (about 3%), ferulic acid (about 10%), glyceryl ethylhexanoate dimethoxycinnamate (about 10%), glycerol para-aminobenzoic acid (about 10%), phenylbenzimidazole sulfonic acid (about 3%) and Parsol SLX (benzylidene malonate polysiloxane), and mixtures thereof. The amounts listed in the preceding list are for each sunscreen individually. In some embodiments in which a combination or mixture of sunscreens is used, the total combined amount of a sunscreen may be less or equal to the sum of the maximum suitable amounts for each individual sunscreen.

As used herein, the term "Cinnamates", include octinoxate, cinoxate, and isoamyl p-methoxy cinnamate.

As used herein, the term "Salicylates" include octisalate, homosalate, and trolamine salicylate.

As used herein, the term "Benzophenones" includes oxybenzone, sulisobenzone, and dioxybenzone.

As used herein, the term "PABA and derivatives" includes PABA (p-aminobenzoic acid), Octyldimethyl PABA (Padimate O), p-amyldimethyl PABA (Padimate A), Ethyl 4[bis (hydroxypropyl)] aminobenzoate, and glyceryl PABA.

Avobenzone, and benzophenones, as well as some other sunscreens, are photo unstable. Therefore these sunscreens are frequently combined with other sunscreens or stabilizers to increase the photostability of the final product. Some suitable photo stabilizers also referred to herein as boosters, include, but are not limited to Octocrylene, Diethylhexyl 2,6-naphthalate, and Diethylhexyl syringylidene malonate. In one embodiment, the photostabilizer is Diethylhexyl syringylidene malonate.

Although a single sunscreen may be used in a composition, typically a combination of sunscreens will be used as each sunscreen has a characteristic wavelength range in which it absorbs UV radiation (UVR) and typically that range is less than the entire range for which protection is desired. Thus, use of a combination of sunscreens provides protection over a wider range of wavelengths. Additionally, efficacy of protection is also related to the amount of sunscreen. As regulatory agencies limit the amount of each sunscreen that can be used, the use of multiple sunscreens improves the SPF while maintaining regulatory compliance.

Organic sunscreens and their efficacious wavelength range (along with suitable amounts) are as follows: amino benzoic acid (260 nm-313 nm, about 5% to about 15%); padimate O (290 nm-315 nm, about 1.4% to about 8%);

dioxybenzone (260 nm-380 nm, about 1% to about 3%); oxybenzone (270 nm-350 nm, about 2% to about 6%); sulisobenzone (260 nm-375 nm, about 5% to about 10%); cinoxate (270 nm-328 nm, about 1% to about 3%); octocrylene (250 nm-360 nm, about 7% to about 10%); Avobenzone (320 nm-400 nm, about 1% to about 3%); octyl salicylate (280 nm-320 nm, about 3% to about 5%); homosalate (295 nm-315 nm, about 4% to about 15%); trolamine salicylate (260 nm-320 nm, about 5% to about 12%); octinoxate (290 nm-320 nm, about 2% to about 7.5%).

In one embodiment, at least two sunscreens are used where the first sunscreen has an efficacious wavelength range that includes about 280 nm to about 315 nm and the second sunscreen has an efficacious wavelength range that includes about 315 nm to about 400 nm.

In one embodiment, the at least one UVA sunscreen is Avobenzone, and/or Diethylamino hydroxybenzoyl hexyl benzoate (Uvinul A Plus).

In an embodiment, the at least one UVB sunscreen is Ethylhexyl triazone (Uvinul T 150), Octyl methoxycinnamate (Octinoxate), and/or Octyl salicylate (Octisalate), alone or in mixtures thereof.

In an embodiment, the at least one sunscreen which is a UVA+UVB filter is Bemotrizinol (Tinosorb S), Iscotrizinol (Uvasorb HEB), Octocrylene, and Bisoctrizole (Tinosorb M), and mixtures thereof.

In one embodiment, the sunfilters include a combination of Bemotrizinol, Diethylamino hydroxybenzoyl hexyl benzoate, isoamyl p-methoxycinnamate, an optionally Tinosorb A2B.

In another embodiment, the sunfilters include a combination of Tinosorb S, Tinosorb M, and Octyl methoxycinnamate.

In another embodiment, the sunfilters include a combination of Tinosorb S, Tinosorb M, Octyl methoxycinnamate, and Uvinul A Plus.

In another embodiment, the at least one lamellar membrane structure comprises (i) a phospholipid present in an amount from about 0.5% to about 2.5% by weight, (ii) a fatty alcohol present in an amount from about 2% to about 10% by weight, and (iii) a fatty acid present in an amount from about 0.5% to about 2.5% by weight, and wherein all percentages are based on the total weight of the composition.

In yet another embodiment, the at least one lamellar membrane structure comprises (i) a phospholipid present in an amount from about 0.5% to about 2.5% by weight, (ii) a fatty alcohol present in an amount from about 2% to about 7.5% by weight, (iii) a fatty acid present in an amount from about 0.25% to about 2.5% by weight, and (iv) an ester of a branched fatty acid and a branched fatty alcohol present in an amount from about 0.25% to about 2.5% by weight, and wherein all percentages are based on the total weight of the composition.

In yet another embodiment, the at least one lamellar membrane structure comprises (i) a phospholipid present in an amount from about 0.5% to about 2.5% by weight, (ii) a fatty alcohol present in an amount from about 2% to about 7.5% by weight, and (iii) an ester of a branched fatty acid and a branched fatty alcohol present in an amount from about 0.25% to about 2.5% by weight, and wherein all percentages are based on the total weight of the composition.

Accordingly, in an embodiment, the invention provides a topical oil-in-water emulsion composition comprising
a) a discontinuous oil phase;
b) a continuous aqueous phase comprising water;
c) a thickening agent;
d) one or more of a monofatty acid ester of glycerin and/or one or more of a monofatty acid ester of glycol, or mixtures thereof; and
(e) at least one lamellar membrane structure comprising (i) a phospholipid present in an amount from about 0.5% to about 5% by weight, and (ii) a fatty alcohol present in an amount from about 2% to about 15% by weight; and
wherein in use the composition has a water vapor transmission rate measured in vitro using the modWVTR test methodology that is less than a composition not containing a monofatty acid ester of glycerin and/or a monofatty acid ester of glycol.

In an embodiment, the composition has a water vapor transmission rate of less than about 70 $g \cdot m^{-2} \cdot hr^{-1}$ measured in vitro using the modWVTR test methodology. In another embodiment, the composition has a water vapor transmission rate of less than about 65 $g \cdot m^2 \cdot hr^{-1}$ measured in vitro using the modWVTR test methodology.

In one embodiment, the invention provides a topical oil-in-water emulsion composition comprising
a) a discontinuous oil phase;
b) a continuous aqueous phase comprising water;
c) a thickening agent;
d) one or more of a monofatty acid ester of glycerin and/or one or more of a monofatty acid ester of glycol, or mixtures thereof; and
e) at least one lamellar membrane structure comprising (i) a phospholipid present in an amount from about 0.5% to about 2.5% by weight, (ii) a fatty alcohol present in an amount from about 2% to about 10% by weight, and (iii) a fatty acid present in an amount from about 0.5% to about 2.5% by weight; and
wherein in use the composition has a water vapor transmission rate measured in vitro using the modWVTR test methodology that is less than a composition not containing a monofatty acid ester of glycerin and/or a monofatty acid ester of glycol.

In another embodiment, the invention provides a topical oil-in-water emulsion composition comprising
a) a discontinuous oil phase;
b) a continuous aqueous phase comprising water;
c) a thickening agent;
d) one or more of a monofatty acid ester of glycerin and/or one or more of a monofatty acid ester of glycol, or mixtures thereof; and
e) at least one lamellar membrane structure comprising (i) a phospholipid present in an amount from about 0.5% to about 2.5% by weight, (ii) a fatty alcohol present in an amount from about 2% to about 7.5% by weight, (iii) a fatty acid present in an amount from about 0.25% to about 2.5% by weight, and (iv) an ester of a branched fatty acid and a branched fatty alcohol present in an amount from about 0.25% to about 2.5% by weight; and
wherein in use the composition has a water vapor transmission rate measured in vitro using the modWVTR test methodology that is less than a composition not containing a monofatty acid ester of glycerin and/or a monofatty acid ester of glycol.

In yet another embodiment, the invention provides a topical oil-in-water emulsion composition comprising:
(a) a discontinuous oil phase;
(b) a continuous aqueous phase comprising water;
(c) a thickening agent;

(d) one or more of a monofatty acid ester of glycerin and/or one or more of a monofatty acid ester of glycol, or mixtures thereof; and
(e) at least one lamellar membrane structure comprising (i) a phospholipid which is hydrogenated phosphatidylcholine, (ii) behenyl alcohol, (iii) behenic acid, and (iv) isostearyl isostearate; and wherein in use the composition has a water vapor transmission rate measured in vitro using the modWVTR test methodology that is less than a composition not containing a monofatty acid ester of glycerin and/or a monofatty acid ester of glycol.

In a further embodiment, the invention provides a topical oil-in-water emulsion composition comprising:
(a) a discontinuous oil phase;
(b) a continuous aqueous phase comprising water;
(c) a thickening agent;
(d) one or more of a monofatty acid ester of glycerin and/or one or more of a monofatty acid ester of glycol, or mixtures thereof; and
(e) at least one lamellar membrane structure comprising (i) hydrogenated phosphatidylcholine, and (ii) a mixture of behenyl alcohol and cetyl alcohol, (iii) behenic acid, and (iv) isostearyl isostearate; and wherein in use the composition has a water vapor transmission rate measured in vitro using the modWVTR test methodology that is less than a composition not containing a monofatty acid ester of glycerin and/or a monofatty acid ester of glycol.

In one embodiment, the invention provides a topical oil-in-water emulsion composition comprising:
(a) a discontinuous oil phase;
(b) a continuous aqueous phase comprising water;
(c) a thickening agent;
(d) one or more of a monofatty acid ester of glycerin and/or one or more of a monofatty acid ester of glycol, or mixtures thereof; and
(e) at least one lamellar membrane structure comprising (i) hydrogenated phosphatidylcholine present in an amount from about 0.5% to about 2.5% by weight, (ii) a fatty alcohol present in an amount from about 2% to about 7.5% by weight, which is a mixture of cetyl alcohol and behenyl alcohol, (iii) a fatty acid present in an amount from about 0.25% to about 2.5% by weight, which is behenic acid, and (iv) an ester of branched fatty acid and a branched fatty alcohol present in an amount from about 0.25% to about 2.5% by weight, which is isostearyl isostearate; and
wherein in use the composition has a water vapor transmission rate measured in vitro using the modWVTR test methodology that is less than a composition not containing a monofatty acid ester of glycerin and/or a monofatty acid ester of glycol and wherein all percentages are based on the total weight of the composition.

In an embodiment, the at least one lamellar membrane structure comprises (i) a phospholipid and (ii) a straight chain $C_{12}$-$C_{36}$ fatty alcohol.

In another embodiment, the at least one lamellar membrane structure comprises (i) a phospholipid, (ii) a straight chain $C_{12}$-$C_{36}$ fatty alcohol, and (iii) a straight chain $C_{12}$-$C_{36}$ fatty acid.

In yet another embodiment, the at least one lamellar membrane structure comprises (i) a phospholipid, (ii) a straight chain $C_{12}$-$C_{36}$ fatty alcohol, (iii) a straight chain $C_{12}$-$C_{36}$ fatty acid, and (iv) an ester of a $C_{12}$ to $C_{30}$ branched fatty acid and $C_{12}$ to $C_{30}$ branched fatty alcohol.

In embodiment, there is a topical oil-in-water emulsion composition comprising:
a) a discontinuous oil phase;
b) a continuous aqueous phase comprising water;
c) a thickening agent;
d) one or more of a monofatty acid ester of glycerin and/or one or more of a monofatty acid ester of glycol, or mixtures thereof; and
e) at least one lamellar membrane structure comprising (i) hydrogenated phosphatidylcholine, and (ii) a mixture of behenyl alcohol and cetyl alcohol, (iii) behenic acid, and (iv) isostearyl isostearate; and wherein in use the composition has a water vapor transmission rate measured in vitro using the modWVTR test methodology that is less than a composition not containing a monofatty acid ester of glycerin and/or a monofatty acid ester of glycol.

In an embodiment, the composition has a water vapor transmission rate of less than about 70 $g \cdot m^{-2} \cdot hr^{-1}$ measured in vitro using the modWVTR test methodology. In another embodiment, the composition has a water vapor transmission rate of less than about 65 $g \cdot m^{-2} \cdot hr^{-1}$ measured in vitro using the modWVTR test methodology. In another embodiment, the composition has a water vapor transmission rate of less than about 60 $g \cdot m^{-2} \cdot hr^{-1}$ measured in vitro using the modWVTR test methodology.

It should be noted that the present formulations do not include as a necessary excipient a traditional surfactant. Thus in one embodiment, the formulations of the present invention can include small amounts, e.g., 0.5%, less than 0.4%, less than 0.3%, less than 0.2%, less than 0.1% w/w, and no 0.0% w/w of a traditional surfactant. As such this is meant an anionic, cationic, non-ionic and zwitterionic surfactant.

Traditional anionic surfactants include ammonium lauryl sulfate, sodium lauryl sulfate (sodium dodecyl sulfate, SLS, or SDS), and the related alkyl-ether sulfates sodium laureth sulfate (sodium lauryl ether sulfate or SLES), docusate (dioctyl sodium sulfosuccinate), perfluorooctanesulfonate (PFOS), alkyl-aryl ether phosphates and alkyl ether phosphates. Traditional cationic surfactants include cetrimonium bromide (CTAB), cetylpyridinium chloride (CPC), and benzalkonium chloride (BAC). Traditional zwitterionic surfactants include cocamidopropyl hydroxysultaine, and cocamidopropyl betaine. Traditional non-ionic surfactants include polyethylene glycol alkyl ethers (such as Brij); polypropylene glycol alkyl ethers; glucoside alkyl ethers, such as decyl glucoside, lauryl glucoside, and octyl glucoside; polyethylene glycol octylphenyl ethers, such as Triton X-100; polyethylene glycol alkylphenyl ethers, such as Nonoxynol-9; Glycerol alkyl esters, such as glyceryl laurate; polyoxyethylene glycol sorbitan alkyl esters, such as the polysorbates; the sorbitan alkyl esters, such as the spams; and the block copolymers of polyethylene glycol and polypropylene glycol, e.g. the poloxamers.

Definitions

As used herein the term "long chain" or "fatty" such as used in reference to "fatty alcohol" or "fatty acid", etc. refers to a hydrocarbon backbone chain which may be straight or branched, saturated or unsaturated, and is suitably composed of 12 to 36 carbon atoms. In one embodiment, the chain is 16 to 26 carbon atoms. In another embodiment the chain is 16 to 22 carbon atoms. In one embodiment, the chain is 22 to 30 carbon atoms. In one embodiment, the chain is 16 to 26 carbon atoms. In another embodiment the chain is 16 to 22 carbon atoms. In another embodiment, the chain is 20 to 22 carbon atoms. In another embodiment, the chain is from 20 to 30 carbon atoms, suitably 22 to 30 carbon atoms. In another embodiment the chain is from 22 to 28 carbon atoms.

The term "applying" as used herein refers to any method which, in sound medical or cosmetic practice, delivers the topical composition to the lips of a subject in such a manner so as to provide a positive effect on a dermatological disorder, condition, or appearance. The compositions are preferably administered such that they cover the entire lips.

As used herein, the phrases an "effective amount" or a "therapeutically effective amount" refers to an amount of a composition or component thereof sufficient enough to have a positive effect on the area of application. Accordingly, these amounts are sufficient to modify the skin disorder, condition, or appearance to be treated but low enough to avoid serious side effects, within the scope of sound medical advice. An effective amount will cause a substantial relief of symptoms when applied repeatedly over time. Effective amounts will vary with the particular condition or conditions being treated, the severity of the condition, the duration of the treatment, and the specific components of the composition being used.

An "effective amount" of a sunscreen is an amount of sunscreen sufficient to provide measurable protection from solar radiation as determined by having a measurable Sun Protection Factor (SPF) value and/or UVA protection value.

The term "SPF" (Sun Protection Factor) means the UVB energy required to produce a minimal erythema dose on sunscreen treated skin divided by the UVB energy required to produce a minimal erythema dose on unprotected skin.

The term "about" means within an acceptable range for the particular parameter specified as determined by one of ordinary skill in the art, which will depend, in part, on how the value is measured or determined, i.e., the limitations of the measurement system. For example, "about" can mean a range of up to 10% of a given value.

As used herein, the phrase "salts thereof" refers to salts that are pharmaceutically acceptable. Such salts include: (1) acid addition salts, formed with acids such as, for example, acetic acid, benzoic acid, citric acid, gluconic acid, glutamic acid, glutaric acid, glycolic acid, hydrochloric acid, lactic acid, maleic acid, malic acid, malonic acid, mandelic acid, phosphoric acid, propionic acid, sorbic acid, succinic acid, sulfuric acid, tartaric acid, naturally and synthetically derived amino acids, and mixtures thereof; or (2) salts formed when an acidic proton present in the parent compound is either (i) replaced by a metal ion e.g. an alkali metal ion, an alkaline earth metal ion, or an aluminium ion; or (ii) protonates an organic base such as, for example, ethanolamine, diethanolamine, triethanolamine, tromethamine and N-methylglucamine.

"%" as used herein, refers to the percentage by weight of the total composition, unless otherwise specified. All percentages are based on the percent by weight of the final composition prepared unless otherwise indicated and all totals equal 100% by weight.

The term "wt/wt" or "by weight", unless otherwise indicated, means the weight of a given component or specified combination of components to the total weight of the composition expressed as a percentage.

As used herein, moles, is a measure of the amount of a chemical species based upon its molecular weight. No. of moles=Mass/Molar Mass Mole % (mol %) is simply the number of moles of a given lamellar forming component used in a formulation relative to the total number of moles of all stated lamellar forming species, expressed as a percentage.

As used herein, the term "phytosterol" refers to plant sterols and plant stanols. Plant sterols are naturally occurring cholesterol-like molecules found in all plants, with the highest concentrations occurring in vegetable oils. Plant stanols are hydrogenation compounds of the respective plant sterols. Phytosterols are natural components of common vegetable oils.

As used herein, the term "sensitive skin" refers to the degree of skin irritation or skin inflammation, as exemplified by parameters in suitable assays for measuring sensitivity, inflammation or irritation.

It should be understood that the terms "a" and "an" as used herein refer to "one or more" of the enumerated components. It will be clear to one of ordinary skill in the art that the use of the singular includes the plural unless specifically stated otherwise.

The term "and/or" as used herein covers both additively and also alternatively the individual elements of a list which are thus linked so that these elements are to be understood as linked selectively with "and" or respectively with "or". Furthermore, the terms used in the singular of course also comprise the plural.

Throughout the application, descriptions of various embodiments use "comprising" language, however in some specific instances, an embodiment can alternatively be described using the language "consisting essentially of" or "consisting of".

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition. As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to an individual and interactions which would result in pharmaceutical compositions that are not pharmaceutically acceptable are avoided. In addition, each excipient must of course be of sufficiently high purity to render it pharmaceutically-acceptable.

"Substantially free" of a specified component refers to a composition with less than about 1% by weight of the specified component. "Free" of a specified component refers to a composition where the specified component is absent.

A designation that a substance is a semisolid, should be taken to mean the physical state of the substance in the temperature range of about 20° C. to about 40° C.

The term "organic sunscreen" means a compound or mixture of compounds that can protect human skin from UVA and/or UVB radiation and is the class of compounds classified by those skilled in the art of chemistry as organic chemicals.

The term "inorganic sunscreen" means a compound or mixture of compounds that can protect human skin from UVA and/or UVB radiation and is the class of compounds classified by those skilled in the art of chemistry as inorganic chemicals. Exemplary inorganic sunscreens include, but are not limited to, zinc oxide and titanium dioxide.

As used herein, "mammal" includes but is not limited to humans, including pediatric, adult and geriatric patients.

The following examples are illustrative of the present invention and are not intended to be limitations thereon.

Other terms as used herein are meant to be defined by their well-known meanings in the art.

Materials and Methods

A high melting point lipid that contains mainly a mixture of glycerides of long chain fatty acids is Compritol ATO 888 (hereinafter "CA8") (J. B. Brubach, et al., Int J Pharm, 336 (2007) 248-256). CA8 is a waxy material widely used to modify drug release behavior from drug matrices (F. Q. Li, et al., International Journal of Pharmaceutics, 324 (2006) 152-157). This lipid mixture can be used as a source of long chain fatty acids and consequently is a suitable starting material to obtain varied derivatives of long chain fatty acid for cosmetic use.

The physical properties and lipid phase packing behavior of behenoyl glycerides were studied using Differential Scanning Calorimetry (DSC), Fourier transform infrared spectroscopy (FT-IR), and Langmuir monolayer studies. These helped to identify the structural functionality require in the glyceryl ester derivatives that form an orthorhombically-packed lipid phase. This data helps substantiate that the innovative lipid of this invention mimic the behavior and lateral packing structures of naturally occurring molecules in SC lipids to provide a technologically-viable replacement to currently-used occlusive materials in skin formulations.

CA8 was obtained from Gattefossé. Solvent and other chemicals were bought from Sigma-Aldrich except for myristic acid and palmitic acid which were bought from Bie&Berntsena-s and FLUKA, respectively. Novozym 435 (*Candida Antarctica* lipase B) was provided by Novozymes A/S (Bagsvaerd, Denmark). Caprylic/capric triglyceride and Phosphatidylcholine (mix of C16 and C18 saturated acyl chains) were bought from BASF, Florham Park, N.J., USA and Lipoid, Newark, N.J., USA, respectively. Pentylene Glycol was obtained from Symrise, Teterboro, N.J., USA. Mp Biomedicals, Solon, Ohio was the supplier used for glycerin. Polymer mixtures were obtained from different suppliers: Xanthan Gum (CP Kelco, Leatherhead, Surrey, UK), Sodium Carbomer (3V Inc., Georgetown, S.C., USA), Carbomer Interpolymer Type A (Lubrizol, Cleveland, Ohio, USA), Hydroxyethycellulose (Ashland Inc., Covington, Ky., USA). NMR spectra were acquired on a Bruker Avance III 400 spectrometer using as solvent deuterated chloroform. HPLC analyses were run for the different glycerides using the following conditions: 70-30% of A in B (A=Acetonitrile and B=isopropanol/hexane 2:1) in 35 min with a flow rate of 1 mL/min using a C-18 column (150×4.0 mm; particle size, 5 μM) on a Thermo Scientific HPLC containing a Finnigan Surveyor LC pump plus also equipped with a Evaporative Light Scattering Detectors (ELSD) detector (SEDEX 80).

Short Path Distillation (SPD)

A KD5 system was used. This equipment consists of a feeding tank, a cylindrical body surrounded by a heating jacket with a rotor and a condenser inside, a residual and a distillate receiver and two vacuum pumps including a diffusion pump. The thermal separation was carried out at $1 \times 10^{-3}$ mbar and the feeding rate used was 100 mL/h. 185° C. was used for distillation of monoglycerides and 265° C. to distill mainly diglycerides, and obtain pure triglycerides in the residue.

Synthesis of Behenoyl Glycerides and Analogues

Glycerol Monobehenate (1): In a coated reactor with a stirring magnet, 1 equivalent (herein after "eq") of behenic acid and 10 eq of glycerol were dissolved in t-butanol at 55° C. Posteriorly, 15% mass of enzyme (Novozym 435) were added. After two hours, the enzyme was filtered off and t-butanol was evaporated down to dryness. Subsequently, the resulting reaction mixture was diluted in chloroform and the unreacted behenic acid was removed using a saturated solution of sodium carbonate. The resulting organic layer was washed 3 times with brine solution, dried over anhydrous sodium sulfate, filtered, and evaporated down to dryness yielding a white solid with a melting point of 77° C.; $^1$H-NMR (400 MHz, $CDCl_3$) δ 4.25-4.09 (m, 2H), 3.97-3.89 (m, 1H), 3.73-3.55 (m, 2H), 2.35 (t, J=7.2 Hz, 2H), 1.70-1.53 (m, 2H), 1.48-1.02 (m, 36H), 0.88 (t, J=6.8 Hz, 3H); HPLC-ELSD: rt=4.79 min (% area=95).

Glycerol dibehenate (2): A similar procedure to the one described for Compound 1 was carried out to obtain Compound 2 but instead 2 eq of behenic acid and 1 eq of glycerol were used to promote the formation of diglyceride (Z.-Q. Duan, et al., Process Biochemistry, 45 (2010) 1923-1927).

Colum chromatography (Hexane:Ethyl acetate 8:2) was required to isolate the desired Compound 2. This yielded a white solid with a melting point of 75° C.; $^1$H-NMR (400 MHz, $CDCl_3$) δ 4.33-3.98 (m, 5H), 2.28 (t, J=7.6 Hz, 4H), 1.65-1.42 (m, 4H), 1.38-0.97 (m, 72H), 0.81 (t, J=7.2 Hz, 6H); HPLC-ELSD: rt=11.05 min (% area=93).

Acetylated glycerol monobehenate (3): Glycerol monobehenate, 12 eq of acetic anhydride and 2.4 eq of trimethylamine were added in a round-bottom flask with a stirring magnet and let react for 24 h at reflux. Following this step, the reaction mixture was dissolved in chloroform and the organic layer was washed with a saturated solution of ammonium chloride, a saturated solution of sodium carbonate, and brine solution. Finally, we dried the organic layer over anhydrous sodium sulfate, filtered, and evaporated down to dryness. $^1$H-NMR (400 MHz, $CDCl_3$) δ 5.31-5.20 (m, 1H), 4.35-4.24 (m, 2H), 4.20-4.10 (m, 2H), 2.31 (t, J=7.6 Hz, 2H), 2.08 (d, J=4 Hz, 6H), 1.68-1.53 (t, 2H), 1.48-1.01 (m, 36H), 0.87 (t, J=7.2 Hz, 3H); HPLC-ELSD: rt=4.18 min (% area=91).

Acetylated glycerol dibehenate (4): A similar procedure to that used to synthesize Compound 3 was followed but using as starting material Compound 2. $^1$H-NMR (400 MHz, $CDCl_3$) δ 5.32-5.20 (m, 1H), 4.37-4.09 (m, 5H), 2.32 (t, J=7.6 Hz, 4H), 2.07 (s, 3H), 1.69-1.49 (m, 4H), 1.47-1.01 (m, 72H), 0.88 (t, J=6.8 Hz, 6H); HPLC-ELSD: rt=11.53 min (% area=90).

Synthesis of asymmetric diglycerides of behenic acid (5a-b): 1 eq of a short chain fatty acid (C8-C18), 20 eq of glycerol were dissolved in t-butanol. Posteriorly, 5% weight of Novozym 435 were added and the reaction ran for 2 hours at room temperature. Subsequently, the enzyme was removed by filtration, the mixture was evaporated down and the reaction mixture was dissolved in DCM. Following, the DCM layer was washed with a saturated aqueous solution of sodium carbonate to remove the fatty acid that did not react. Later, the organic layer was washed with a saturated aqueous solution of sodium chloride, dried over anhydrous sodium sulfate, filtered, and evaporated to dryness. Finally, 2 eq of the resulted monoglyceride, 1 eq. behenic acid, 1 eq. of EDC (1-Ethyl-3-(3-dimethylaminopropyl)-carbodiimide), 0.4 eq. of DMAP (4-Dimethylaminopyridine) were made react in DCM at 40° C. for 45 mins. After 45 minutes had elapsed, the reaction mixture was diluted in DCM and washed off with a saturated aqueous solution of ammonium chloride, a saturated solution of sodium carbonate, and brine solution. Later, the organic layer was dried over anhydrous sodium sulfate, filtered, and evaporated to dryness and the resulting solid was dissolved in hexane and the unreacted monoglyceride was washed off with 80% Ethanol in water. If necessary column chromatography was carried out using 8:2 Hexane:Ethyl acetate as eluent.

2-hydroxy-3-(octanoyloxy)propyl docosanoate (5a): White solid with a melting point of 57° C.; 1H-NMR (400 MHz, $CDCl_3$) δ 4.25-4.04 (m, 4H), 2.35 (t, J=7.5 Hz, 4H), 1.68-1.52 (m, 4H), 1.36-1.20 (m, 42H), 0.95-0.83 (m, 6H); HPLC-ELSD: rt=5.23 min (% area=90.4)

3-(decanoyloxy)-2-hydroxypropyl docosanoate (5b): White solid with melting point of 66° C.; 1H-NMR (400 MHz, $CDCl_3$) δ 4.24-4.03 (m, 5H), 2.35 (t, J=7.6 Hz, 4H), 1.69-1.59 (m, 4H), 1.27 (m, 48H), 0.89 (t, J=6.4 Hz, 6H); HPLC-ELSD: rt=5.73 min (% area=97). 3-(dodecanoyloxy)-2-hydroxypropyl docosanoate (5c): White solid with melting point of 68° C.; 1H-NMR (400 MHz, $CDCl_3$) δ 4.22-4.05 (m, 4H), 2.35 (t, J=7.6 Hz, 4H), 1.67-1.58 (m, 4H), 1.27 (m, 51H), 0.89 (t, J=6.4 Hz, 6H); HPLC-ELSD: rt=6.15 min (% area=96).

2-hydroxy-3-(tetradecanoyloxy)propyl docosanoate (5d): White solid with melting point of 69° C.; 1H-NMR (400 MHz, $CDCl_3$) δ 4.22-4.05 (m, 6H), 2.35 (t, J=7.6 Hz, 4H), 1.67-1.60 (m, 4H), 1.27 (m, 56H), 0.93-0.82 (m, 6H); HPLC-ELSD: rt=6.85 min (% area=93).

2-hydroxy-3-(palmitoyloxy)propyl docosanoate (5e): White solid with melting point of 74° C.; 1H-NMR (400 MHz, $CDCl_3$) δ 4.23-4.06 (m, 2H), 2.35 (t, J=7.6 Hz, 4H), 1.68-1.57 (m, 4H), 1.27 (m, 60H), 0.89 (t, J=6.4 Hz, 6H); HPLC-ELSD: rt=7.97 min (% area=98).

2-hydroxy-3-(stearoyloxy)propyl docosanoate (5f): White solid with melting point of 64° C.; 1H-NMR (400 MHz, $CDCl_3$) δ 4.23-4.05 (m, 5H), 2.35 (t, J=7.6 Hz, 4H), 1.67-1.58 (m, 4H), 1.27 (m, 71H), 0.89 (t, 6.4 Hz, 6H); HPLC-ELSD: rt=8.55 min (% area=97).

Ethyleneglycol monobehenate (6): A chemical coupling was carried out using EDC/DMAP at 40° C. and ethylene glycol and behenic acid as starting materials. Subsequently, the reaction mixture was dissolved in DCM, washed with a saturated solution of $Na_2CO_3$, dried over anhydrous $Na_2SO_4$, and evaporated down. The resulted mixture was dissolved in hexane and washed with a solution of ethanol 80% This yielded a white solid with melting point of 71° C.; 1H-NMR (400 MHz, $CDCl_3$) δ 4.24-4.15 (m, 2H), 3.85-3.77 (m, 2H), 2.33 (t, J=7.6 Hz, 2H), 1.94 (b, 1H), 1.69-1.55 (m, 2H), 1.48-1.03 (m, 36H), 0.89 (t, J=6.4 Hz, 3H); HPLC-ELSD: rt=4.54 min (% area=98).

Differential Scanning Calorimetry (DSC)

DSC equipment Perkin-Elmer Cetus, Norwalk, USA was used to analyze the thermal properties of the different behenoyl lipids. In an aluminum pan 8-12 mg of the lipid of interest was sealed and placed into the DSC system under a purging nitrogen atmosphere of 20 mL/min. A scan speed of 5° C. per min was used for cooling and heating runs in the temperature range between −60° C. to 90° C. The DSC scans were analyzed using the MicroCal Origin 8.6 software.

Fourier Transform Infrared Spectroscopy (FT-IR)

FT-IR spectra were acquired using a Q-interline FTLA2000-154 with PIKE Technologies MIRACLE™ single reflection horizontal ATR. All spectra were recorded at room temperature and derivatized using a Savitsky-Golay algorithm.[43] Samples analyzed by FT-IR were previously melted and cooled down.

Langmuir Film and Atomic Force Microscopy

To carry out Langmuir-Blodgett studies following a similar procedure to that reported Correa et al.[44] Monolayer measurements were performed out using a solution of 150 mM sodium chloride and 1 mM ethylenediamine tetraacetic acid (EDTA) tetrasodium salt at pH 5.5. Generally less than 20 mL of an approximately 2 mg/mL solution of lipid in chloroform:methanol (9:1) were spread on the water surface and solvent allowed to evaporate for a period of 20 minutes. Subsequently, the monolayer was compressed at a constant rate of ~9 $Å^2$/chain/min until collapse. After the conditions were set, the deposition of monolayers was carried out on a mica plate, at a pressure just before the film has collapsed, for AFM studies. AFM measurements were conducted in ambient air under a tapping mode. A silicon tip on a micro cantilever (Olympus Inc., Japan) with spring constant 26 N/m and resonant frequency of 300 kHz was used for the measurements. Samples were analyzed in duplicate.

Formulation Manufacture in a Simple Emulsion Vehicle

A simplified base formulation was utilized to screen a number of putative occlusive lipids as detailed in Table 1. Manufacture was conducted on a 10 g scale using an IKA digital T25 Ultra Turrax homogenizer (Wilmington, N.C., USA) equipped with a small-scale rotor stator attachment. The oil phase, with the putative occlusive agent of interest at 3% w/w, was heated to 85° C., and the aqueous phase to 75° C. The aqueous phase was added to the oil phase and the mixture homogenized at 13,000 rpm for several minutes until a temperature of 55° C. was reached. The polymers were then added and the system homogenized to 50° C., after which the emulsion vessel was placed in a secondary vessel containing freshly drawn water to aid cooling whilst homogenizing to a temperature of 25-30° C. The vessel containing the emulsion was weighed and losses attributable to water evaporation were corrected. A final homogenization was conducted and the systems stored at ambient laboratory conditions for a period of 24 hours prior to further study.

TABLE 1

Formulation details for a simplified emulsion system (SP) used to evaluate lipids.

| INCI Name | % w/w |
| --- | --- |
| Caprylic/capric triglyceride (Myritol 312) | 17.00 |
| Putative occlusive agent | 3.00* |
| Phosphatidylcholine (mix of C16 and C18 saturated acyl chains) (Phospholipon 90H) | 1.50 |
| Water | 62.86 |
| Pentylene Glycol | 5.00 |
| Glycerin | 10.00 |
| Thickening agents ** | 0.64 |

*A petrolatum control cream was also prepared at 10% w/w. In this case the capric/capiylic triglycerides were lowered accordingly.
** can include carbomers and water soluble polymers Using the simplified emulsion system of Table 1, various additional combinations of excipients were added Formulation no. 2 is SP+3% of a triacylglyceride mixture of C22 acyl chains Formulation no. 3 is SP+3% acylated monacylglycerides with a C22 acyl chain Formulation no. 4 is SP+3% acylated monacylglyceride mixture with a C22 acyl chain synthetic (more monodisperse chain length)

Formulation no. 5 is SP+3% acylated monacylglycerides with a C22 acyl chain as a fractionate (more polydispersity in terms of the chain length)

Formulation no. 6 is SP+3% diacyl glyceride mixture with a C22 acyl chain

Formulation no. 7 is SP+3% acylated diacylglyceride mixture of C22 acyl chain

Formulations 2-7 were all prepared by the same method as described herein for the simplified system of Table 1.

Formulation 8 was prepared using as follows:
1. Add all components (except polymer) to a reaction vessel and heat to 85° C. (+/−3° C.).
2. Add polymer and homogenize at 12,000 rpm until a temperature of 60° C. is reached.
3. Place reaction vessel in a water bath of freshly drawn water. Homogenize and cool composition to a temperature of 40° C.
4. Adjust pH to 5.5 (+/−0.3).
5. Added water to compensate for evaporative losses.
6. Re-homogenize for 2 minutes.

Formulation 8:

| Ingredients | 8 |
|---|---|
| Caprylic/capric triglyceride | |
| Diacaprylyl carbonate | 2.50 |
| Cetyl alcohol | 1.50 |
| Phosphatidylcholine | 1.25 |
| Isostearyl isostearate | 0.90 |
| Behenic acid | 0.90 |
| Glyceryl monobehenate | 4.25 |
| Water | 67.90 |
| Glycerin | 10.00 |
| Hydroxyacetophenone | 0.50 |
| Pentylene glycol | 5.00 |
| Sodium hyaluronate | 0.10 |
| Niacinamide | 3.00 |
| D-Panthenol | 1.40 |
| Trisodium ethylenediamine disuccinate | 0.10 |
| Polyacrylate crosspolymer-6 | 0.50 |
| Hydroxyethyl acrylate/ sodium acryloyldimethyl taurate copolymer | 0.20 |
| | 100.0 |
| Observed WVTR (g.m$^{-2}$ · hr$^{-1}$) | 67.32 |

Mass of Formulation #8

| Lamellar Ingredients | Mol Wt | 8 |
|---|---|---|
| Cetyl alcohol | 242.441 | 1.5 |
| Phosphatidylcholine | 790.15 | 1.25 |
| Isostearyl isostearate | 536.96 | 0.9 |
| Behenic acid | 369.3099 | 0.9 |
| Behenyl alcohol | 322.6 | |
| Glyceryl Monobehenate | 414.662 | 4.25 |

Moles of Formulation #8

| Ingredients | Mol Wt | 9 |
|---|---|---|
| Cetyl alcohol | 242.441 | 6.19E−03 |
| Phosphatidylcholine | 790.15 | 1.58E−03 |
| Isostearyl isostearate | 536.96 | 1.68E−03 |
| Behenic acid | 369.3099 | 2.44E−03 |
| Glyceryl Monobehenate | 414.662 | 1.02E−02 |
| Total Moles | | 2.21E−02 |

Mol % of Formulation #8

| Mol %'s | Mol Wt | 8 EE794531/J |
|---|---|---|
| Cetyl alcohol | 242.441 | 27.96 |
| Phosphatidylcholine | 790.15 | 7.15 |
| Isostearyl isostearate | 536.96 | 7.57 |
| Behenic acid | 369.3099 | 11.01 |
| Behenyl alcohol | 322.6 | 0 |
| Glyceryl Monobehenate | 414.662 | 46.31 |
| | | 100 |

Water Vapor Transmission Rate (WVTR)

The ability of the compositions to form an occlusive layer on the skin was evaluated by measuring the water vapor transmission rate (WVTR). The following method, based upon Pennick et al., Intl J Cosmetic Sci, 2012, 34, p 567-574, and G. Pennick, et al., Int J Cosmet Sci, 32 (2010) 304-312; with minor changes as noted below was used. This method is referenced herein (and in the claims) as "modWVTR test methodology".

1. Vitro-Skin (IMS Inc., Portland, Me.) was cut into circular discs using a hole-punch. The discs were weighed on an analytical balance (not Vitro-Corneum as in the Pennick et al. paper.)
2. The discs were taped on opposing edges, rough side up, with adhesive tape and fixed to the glass surface of a pneumatic drive (Byko Drive). A weighted bar was placed on the drive arm and a 50 μm gauge block placed in front of the weighted bar.
3. The test cream was applied in front of the gauge block, such that when the pneumatic arm is actuated a thin film of cream is applied to the surface including the taped Vitro-Skin disc. Typically 4 discs were coated in a single pass of the arm. The button was depressed and the first coat of the disc occurred. The coated discs were left for 8-10 minutes.
4. The adhesive tape was carefully removed and the discs placed onto a mesh drying tray at room temperature. The surface of the drive unit was cleaned and then the process (steps 1-3) repeated for the next samples.
5. Once all the samples had received their initial coat of cream, the first (and most dry samples) was secured in place for a second application of cream perpendicular to the first coat. The discs were then removed and allowed to partially dry for 60 minutes. The process was repeated for the other samples.
6. The coated discs were reweighed and the weight of applied cream determined.
7. Following partial drying, the WVTR cells were filled with 190 sL of deionized water. The discs were then secured in place over the water, coated side up, using the upper portion of the WVTR cell which was screwed into place. The loaded cells were then reweighed to give the initial weight. The WVTR cells are commercially available Payne Cells from SMS (Surface Measurement Systems, UK).

8. The WVTR cells were placed in a desiccator over silica gel desiccant. Relative humidity was typically 24-28% RH. The cells were removed periodically.

9. Weight values were determined over a 45-240 minute period. WVTR was calculated using the standard WVTR formula described by Pennick et al (Intl J Cosmetic Sci, vol. 34, pp 567-574, 2012). Non-normalized WVTR values were obtained.

The WVTR value was calculated over a period of 45-180 minutes using Formula 1:

$$WVTR(g \cdot m^{-2} \cdot hr^{-1}) = \frac{\text{Water Loss (g) } (W_{0.75} - W_{3.0})}{\text{Area of Membrane (m}^2) \times \text{Time (h)}} \quad \text{Formula 1}$$

The area of the membrane was $1.22 \times 10^{-4}$ m$^2$. $W_{0.75}$ and $W_{3.0}$ were the WVTR cell weights in grams at the 0.75 and 3 hour time points respectively. Samples were measured at least in triplicate.

All samples were compared to a blank and 100% petroleum jelly (PJ) controls. PJ was chosen as the positive control as it has been consistently proven to be an occlusive agent in WVTR testing (Pennick, et al., Int J Cosmet Sci, 32 (2010) 304-312).

Statistical Methods

All data was collected in Microsoft Excel before being transferred to GraphPad Prism 5 (GraphPad Software, San Diego, Calif., U.S.A.). Data were checked for normality using the D'Agostino and Pearson omnibus normality test, and then ANOVA tests with subsequent post-hoc comparisons were made using the Bonferroni test, and Dunnet's test. Statistical significance was set at 95%.

Results and Discussion

Short Path Distillation (SPD). Table 2 displays the fatty acid composition of CA8, and as noted this material contains mainly behenoyl glycerides. CA8 was fractionated using SPD. The optimal conditions used to separate the desired glycerides were a temperature of 185° C. with a feed rate of approximately 100 mL/h, and vacuum pressure of $1 \times 10^{1-3}$ mbar to distill monoglycerides (FGMB). At temperature of 265° C., a vacuum pressure of $1 \times 10^{-3}$ mbar and feed rate of 100 mL/h, diglycerides (FGDB) were distilled and triglycerides (FGTB) were collected in the residual receiver. According to HPLC results, fractionated monoglycerides, diglycerides, and triglycerides were obtained with an approximate purity of 91%, 96%, 99%, respectively where the fatty acids were equally distributed in each sample.

TABLE 2

Fatty acid composition of Compritol ATO 888.

| Fatty acyl chain | Percent (%) in Compritol ATO 888 |
|---|---|
| C14:1 | 0.29 |
| C16:0 | 0.67 |
| C18:0 | 3.12 |
| C20:0 | 4.59 |
| C20:2 | 0.12 |
| C20:4 | 0.56 |
| C22:0 | 88.7 |
| C22:1 | 0.09 |
| C24:0 | 1.86 |

Synthesis of Behenoyl Lipids Glycerol monobehenate 1, glycerol dibehenate 2 were synthesized using Novozym 435 (see Scheme 1). The acetylated glycerides 3-4 were obtained through the reaction of the respective glyceride with acetic anhydride while refluxing. In addition, a series of asymmetric diglycerides containing a shorter fatty acid chain (C8-C18) and a behenoyl chain were synthesized. First, the different monoglycerides were obtained by carrying out an esterification reaction using Novozym 435 and an excess of glycerol and later the resulting monoglycerides were respectively coupled to behenic acid using EDC/DMAP as coupling reagents to synthesize the glyceryl derivatives 5a-f. All asymmetric diglycerides were obtained in relatively good yields but no correlation was found between the yield of the reaction and the length of the fatty acid chain of the monoglyceride previously synthesized. However, as expected when analyzing the different derivatives by reverse-phase HPLC, diglycerides containing longer fatty acyl chains displayed longer retention times (5f>5e>5d>5c>5b>5a). In addition, an analogue of glycerol monobehenate was synthesized which contain acylated ethylene glycol instead of acylated glycerol to evaluate if decreasing the number CH—OH functional group has an effect on the occlusive properties of behenoyl lipids. Accordingly, Compound 6 was synthesized in good yields using EDC/DMAP.

Scheme 1 describes the synthesis of derivatives of behenic acid: a) Syntheic pathway of behenoyl glycerides; b) synthetic procedure followed to obtain asymmetric diglycerides containing a C22 fatty acid and a shorter fatty acid chain (C8-C18); and c) Chemical coupling carried out to obtain ethylene glycol monobehenate.

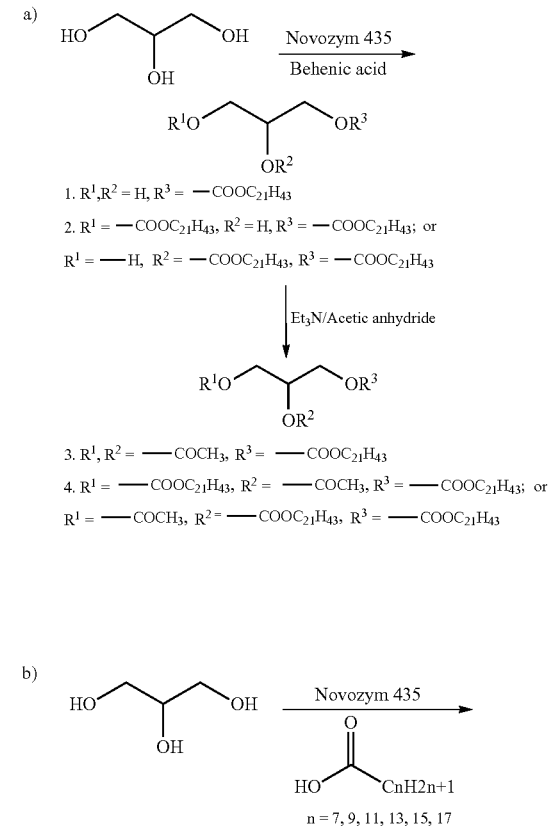

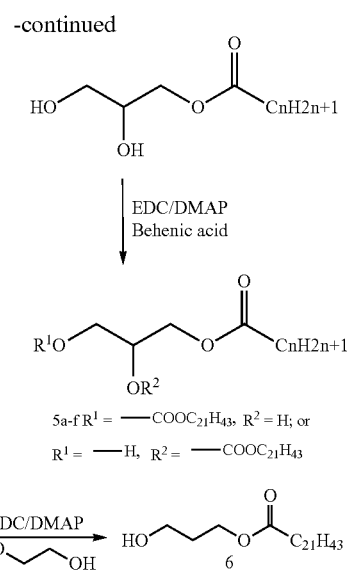

Differential Scanning Calorimetry (DSC) Characterization

As shown in Table 3 below, all glycerides presented melting points below 80° C. Monoglycerides from CA8 presented a higher melting point (mp=79° C.) than diglycerides from CA8 (mp=71-74° C.), and triglycerides from CA8 (mp=68° C.). According to DSC results, both FGMB and FGDB displayed two melting transitions suggesting the existence of a mixture of isomers; 1-monoglyceride and 2-monoglyceride and 1,2-diglyceride and 1,3-diglyceride, respectively. Furthermore, the melting points of the lipids decreased with increasing number of fatty acyl chains. For instance, synthetic glyceryl monobehenate 1 presented a higher melting point (mp=77° C.) than glyceryl dibehenate 2 (mp=75° C.). The latter is believed to be explained by the stronger hydrogen bond interactions between molecules leading to higher the melting points. Thus, acetylation of Compound 1 also generated a molecule with lower melting point (Compound 3: mp=53° C.) than the original molecule. In the case of the asymmetric diglycerides 5, molecules displayed melting points between 57 and 74° C. and the melting point of the derivatives were shown to slightly increase as one of the fatty acid chain increases in length from C8 to C18. The latter is expected since the Van der Waals interactions become stronger with increasing length of the fatty acid chain and more energy is required to break these non-covalent bonds. In addition, Compound 6 (mp=71° C.) displayed a lower melting point than FGMB and synthetic glycerol monobehenate 1 suggesting a less organized packing behavior to that observed for monoglycerides since less energy is required to melt Compound 6. Therefore, based on DSC data mono-acylated glycerol would believe to display better packing behavior than the rest of these behenoyl lipids utilized herein.

FT-IR Characterization

FT-IR spectroscopy studies provided yet another way to understand the molecular organization of the different lipids esters derived from behenic acid. Accordingly, FT-IR can predict the transition between fully extended all-trans hydrocarbon chain to disordered chains since this yields a frequency increase in both symmetric and asymmetric stretching, at ~2850 and 2920 $cm^{-1}$, respectively (D. J. Moore, et al., Acta Derm Venereol Suppl (Stockh), 208 (2000) 16-22). As shown in Table 3, all the behenoyl lipids displayed both peaks corresponding to the symmetric and asymmetric stretching of the fatty acyl chain at ~2850 and 2920 $cm^{-1}$, correspondingly, suggesting the presence of fully extended all-trans fatty acyl chains. In addition, FT-IR provided an insight into the lateral acyl chain packing (M. Boncheva, et al., Biochim Biophys Acta, 1778 (2008) 1344-1355). FT-IR spectroscopy can yield information about orthorhombic, hexagonal, or fluid packing of the lipids. The most organized phase is orthorhombic packing, where all alkyl chains display an all-trans conformation organized in a highly dense rectangular crystalline lattice. FT-IR data suggest that CA8, FGMB, FGDB, Compound 1 and 2 and 6 exhibit orthorhombic packing. However, CA8 and Compound 2 show a mixture of hexagonal and orthorhombic phase, since one of the peaks in the 740-700 $cm^{-1}$ region of the FT-IR spectrum is significantly smaller than the other. The former results can be explained by CA8 being a mixture of glycerides. HPLC analysis shows that it is composed of approximately 13% monoglycerides, 55% diglycerides, and 32% triglycerides. Compound 2 is a compound with two isomers, both of which may affect its ability to pack less tightly.

Multi-acylation of the hydroxyl groups in the glycerol molecule seems to also have a negative impact on the way glycerides pack since FT-IR results for FGTB, and Compound 3, and asymmetric diglycerides 5a-f suggest that all these molecules exhibit hexagonal packing. Conversely, monoacylation promotes tighter packing as demonstrated by FGMB, glycerol monobehenate 1 and Compound 6. Accordingly, these results suggest that glycerol monobehenate, and perhaps the dibehenate as well as ethylene glycol monobehenate might present occlusive characteristics. Thus, a skin care formulation system composed of these lipids was designed to see if they reduced water vapor transmission loss.

TABLE 3

Characterization data of behenoyl lipids.

| Compound | Melting point | FT-IR (740-700 $cm^{-1}$ Region) | Vibrational modes (3000-2800 $cm^{-1}$ Region) | |
|---|---|---|---|---|
| | | | $CH_2$ symmetric stretching | $CH_2$ asymmetric stretching |
| CA8 | 72 | Double peak-Orthorhombic | 2849 | 2916 |
| FGMB | 79 | Double peak-Orthorhombic | 2849 | 2916 |
| FGDB | 71-74 | Double peak-Orthorhombic | 2849 | 2916 |
| FGTB | 68 | Single peak-Hexagonal | 2849 | 2196 |
| 1 | 77 | Double peak-Orthorhombic | 2848 | 2916 |
| 2 | 75 | Double peak-Orthorhombic | 2849 | 2914 |
| 3 | 53 | Single peak-Hexagonal | 2848 | 2914 |
| 4 | 69 | Single peak-Hexagonal | 2849 | 2914 |
| 5a | 57 | Single peak-Hexagonal | 2849 | 2914 |
| 5b | 66 | Single peak-Hexagonal | 2849 | 2912 |
| 5c | 68 | Single peak-Hexagonal | 2849 | 2912 |
| 5d | 69 | Single peak-Hexagonal | 2849 | 2913 |
| 5e | 64-74 | Single peak-Hexagonal | 2849 | 2915 |
| 5f | 64-69 | Single peak-Hexagonal | 2849 | 2916 |
| 6 | 71 | Double peak-Orthorhombic | 2849 | 2916 |

Langmuir Monolayer Studies

Figure 2:
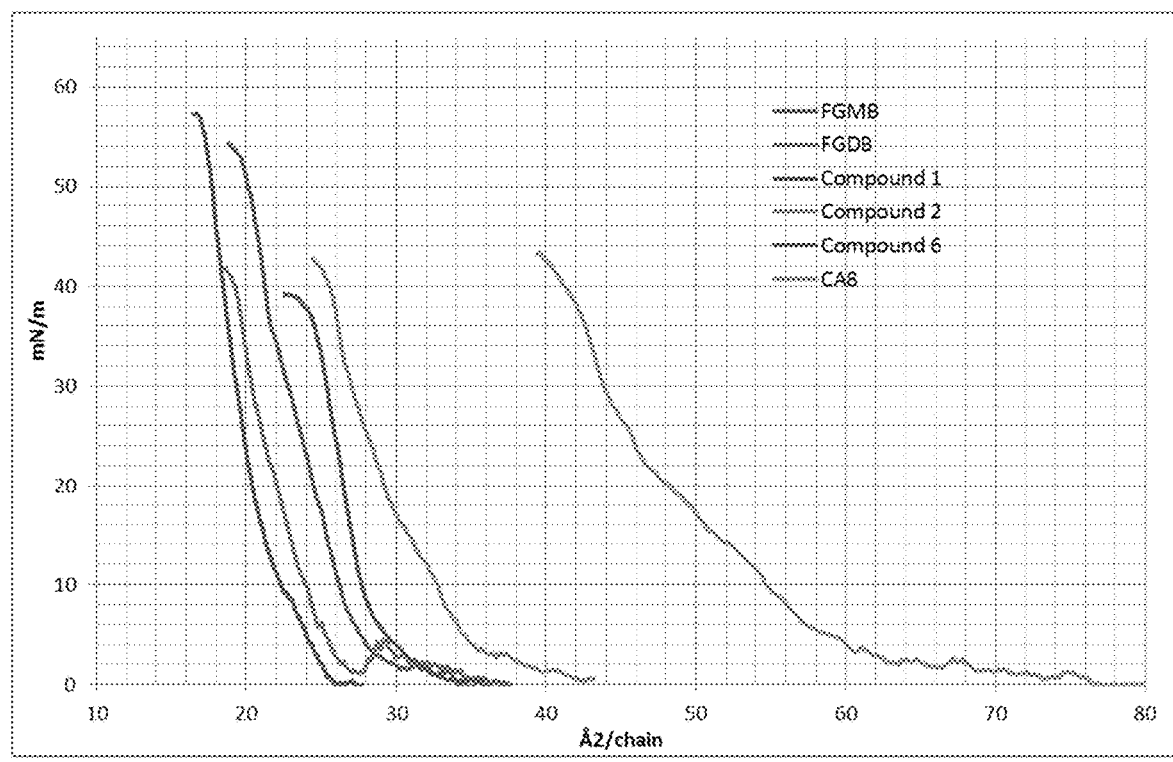
FIG. 2 shows surface pressure-area isotherms of lipids on aqueous surface containing 150 mM NaCl and 1 mM EDTA at pH 5.5.

To better understand the packing behavior of these behenoyl lipids, CA8, Compounds 1, 2, 6 and FGMB and FGDB monolayers were further studied in the Langmuir-Blodgett apparatus and compared with CA8. This approach provides information about i) the stability of the film that a compound can form (the higher final pressure, the higher stability); ii) how well the lipids organize (the bigger the difference between initial and final area, the better compression characteristics the given lipid exhibits); and iii) how densely molecules pack when restricted in a two dimensional system (the smaller Area$_{Final}$, the closer are the lipids chain to each other). These attributes are deemed important in generating an occlusive structure, in particular the ability to densely pack together, since this would suggest a greater ability to act as a diffusional barrier to water loss and generate an occlusive topical product. As shown in FIG. 2 and Table 4, Langmuir monolayer results are in agreement with FT-IR data since glyceryl dibehenate 2 results in a less well packed monolayer than the monobehenate compounds evaluated (FGMB and Compound 1 and Compound 6). This is further demonstrated by the difference between the final and initial area per chain; one of the largest difference is seen with glycerol dibehenate 2 (Area$_{Final-Initial}$=17.5 Å$^2$/chain) among the evaluated compounds. On the other hand, glycerol monobehenate 1 displayed the lowest Area$_{Final}$ (Area$_{Final}$=17 Å$^2$/chain) and the highest collapsing pressure (Pressure$_{Final}$=58 mN/m) suggesting a tighter lateral packing and higher stability. However, at the collapsing pressure, the final area should be equal or approximate to the cross section of the molecule (i.e. the cross-section of the cylindrical fatty acyl chain is 19 Å$^2$) and the final area per chain of Compound 1 resulted 17 Å$^2$ which is lower than expected. This result advocates that the glycerol monobehenate 1 might have started to form double-layers at a pressure higher than 30 mN/m. In addition, as observed in FIG. 1 and Table 3, FGMB presented a less stable and less organized monolayer than Compound 1. The latter is expected since FGMB is a less pure form of glycerol monobehenate containing shorter fatty acyl glycerides which might affect the ability of FGMB to present a more organized and stable monolayer as shown by the final pressure and difference between initial and final area per chain of the evaluated material (Pressure$_{Final}$=53 mN/m and Area$_{Initial-Final}$=14 Å$^2$/chain) compared to the values obtained for Compound 1 (Pressure$_{Final}$=57 mN/m and Area$_{Initial-Final}$=9 Å$^2$/chain). Moreover, Langmuir film studies showed that removal of a hydrogen donor does not favor the formation of monolayer as demonstrated by results found for Compound 6 which displayed a significantly lower collapsing pressure (P$_{Final}$=39 mN/m) and final area per chain (Area$_{Final}$=23 Å$^2$/chain) as compared to Compound 1. As shown in Table 4, FGDB displayed a more organized monolayer than its pure form (Compound 2). For instance, though FGDB displayed the same collapsing pressure (P$_{Final}$=40 mN/m) as its pure form, Compound 2; however, FGDB presented a smaller final area per chain (Area$_{Final}$=19 Å$^2$/chain). The latter might be explained by the fact that FGDB also contains small fractions of FGMB which might be improving the packing behavior. Furthermore, CA8 displayed the worst packing behavior of all studied materials as it presented the biggest difference between the initial and final area per chain (Area$_{Initial-Final}$=37 Å$^2$/chain). Accordingly, Langmuir monolayers results suggest that FGMB and Compound 1 are the most promising compounds of the evaluated series of behenoyl lipids to try and generate skin occlusive products.

FIG. 2 as referenced above demonstrates Surface pressure-area isotherms of lipids on aqueous surface containing 150 mM NaCl and 1 mM EDTA at pH 5.5.

TABLE 4

Langmuir film results of behenoyl lipids.

| | Langmuir monolayer studies | | | |
|---|---|---|---|---|
| Compound | Area$_{Initial}$ (Å$^2$/chain) | Area$_{Final}$ (Å$^2$/chain) | Area$_{Initial}$ − Area$_{Final}$ (Å$^2$/chain) | Pressure$_{Final}$ (mN/m) |
| CA8 | 76 | 39 | 37 | 40 |
| FGMB | 34 | 20 | 14 | 53 |
| FGDB | 28 | 19 | 9 | 40 |
| 1 | 26 | 17 | 9 | 57 |
| 2 | 42.5 | 25 | 17.5 | 40 |
| 6 | 33.5 | 23 | 10.5 | 39 |

Atomic Force Microscopy Imaging

FGMB and Compound 1 were identified as the most potentially occlusive behenoyl lipids when evaluated by the Langmuir monolayer and FT-IR studies. They were further evaluated by AFM imaging after film deposition on mica substrate. The films appeared uniform. However, the monolayer of Compound 1 also displayed regions with 3 nm and 4.5 nm of thickness suggesting that there are areas in the film where the molecule is fully extended or perhaps forming a double layer structure. The latter is in agreement with Langmuir monolayer studies since at pressures higher than 34 mN/m, the film yields an area/chain (Area$_{Final}$<19 Å$^2$/chain) lower than the typically area/chain expected for the cross-section of the cylindrical fatty acyl chain (Area$_{Final}$=19 Å$^2$/chain). Moreover, Fast Fourier transform filtering (FFTF) of the AFM images were also used since this a powerful tool for image analysis. Fourier images reflect repeated patterns as narrow peaks, the co-ordinates of which describe their periodicity and direction. Such peaks are easy to detect by image processing without any pre-knowledge of the features form or periodicity.

Compound 1 showed a striped pattern after FFTF reflecting a property of the system rather than results of the imaging process. This type of striped pattern was previously observed for lignoceric acid (C24). However, FGMB did not display such a pattern. Accordingly, it could be inferred that in the case of FGMB, the shorter chain monoglycerides present in the mixture might be intercalating in between the molecules of glycerol monobehenate and may in turn help generate a more occlusive mixture of lipids.

Water Vapor Transmission Rate (WVTR)

Eleven formulations were made, including a no treatment blank control and 2 petrolatum jelly (PJ) formulations to serve as positive controls as PJ has consistently produced full occlusion in these types of tests. The results of these formulations in the WVTR test are shown in FIG. 1. WVTR is an in-vitro method that estimates water permeation through a polymer film that mimics skin properties (Vitroskin). The polymer film is coated with an emulsion formulation incorporating the lipid of interest. All formulations except CA8 were significantly superior to the blank control. All synthesized and fractionated compounds performed better than CA8 (WVTR=101 g·m$^{-2}$ hr$^{-1}$) as predicted by the Langmuir monolayer studies. FGMB presented a WVTR (51 g·m$^{-2}$ hr$^{-1}$) which is comparable to that of a similar formulation that instead contains 10% petrolatum (47 g·m$^{-2}$ hr$^{-1}$) and was significantly less in allowing water vapor transmission than one containing 3% petrolatum ($P<0.001$). FGMB displayed a lower WVTR than glycerol monobehenate 1 (WVTR=64 g·m$^{-2}$ hr$^{-1}$; $P<0.05$) which suggests that a mixture of glycerides containing mainly glycerol monobehenate offers a more occlusive system than the pure behenoyl lipid 1. This also seems to be in keeping with the FFTF data. Comparing FGMB, which displayed a WVTR=51 g·m$^{-2}$ hr$^{-1}$, to FGDB (WVTR=76 g·m$^{-2}$ hr$^{-1}$) and FGTB (WVTR=94 g·m$^{-2}$ hr$^1$), it can be observed that as the number of hydrogen bond donor decreases, the material becomes less occlusive. FGMB was significantly different to both its di- and triglyceride fractions (P<0.001). The latter is in agreement with DSC data which show that hydrogen bond interactions promoted a tighter packing behavior and a higher melting point. In addition, as predicted by FT-IR and DSC data, Compound 3 (WVTR=90 g·m$^{-2}$ hr$^{-1}$) was significantly less occlusive than glycerol monobehenate 1 (WVTR=64 g·m$^{-2}$ hr$^{-1}$; P<0.001). Moreover, as inferred from Langmuir monolayer studies and DSC data, Compound 6 displayed a numerically but not statically significantly higher WVTR (WVTR=70 g·m$^{-2}$ hr$^{-1}$) than Compound 1 suggesting that decreasing the number of CH—OH functional groups has a negative effect on the occlusive properties of behenoyl lipids. Formulation 8 provided WVTR of about of about 65-70 g·m$^{-2}$ hr$^{-1}$ (not in FIG. 1) Since Compound 1 is composed of 96% glycerol monobehenate and FGMB is composed of approximately 88% of behenoyl lipids with the remaining 12% being glycerides of shorter fatty acyl chain (See Table 2), the better occlusive properties displayed by FGMB could suggest that the shorter fatty acyl lipids might be filling regions between the long-chain behenoyl lipids that may be less tightly packed. The WVTR results illustrate and identify occlusive fatty amphiphiles that exhibit lateral packing characteristics similar to SC lipids.

It is difficult to find sustainable and commercially viable sources of occlusive materials that possess physical attributes similar to lipids found in human SC without having significant safety issues. Such occlusive fatty amphiphiles are thus of great potential value in the treatment of xerotic skin conditions where an established approach to treatment is to occlude the skin. The studies herein demonstrate that fractionated and synthetic behenoyl monoglycerides can decrease WVTRs which in turn, can improve skin barrier function due to their ability to form tightly packed, lateral assemblies. The data further suggest that other long chain monoglycerides either alone, or in combination, may have value in improvement in skin barrier function. FGMB is approximately 88% glyceryl monobehenate along with associated species of longer and shorter acyl chain length. These monoglycerides gave a marked reduction in the WVTR superior to a 3% petrolatum-containing formulation and was comparable to that of 10% petrolatum one. Mechanistically, the results suggest that the ability of glycerides' to act as hydrogen bond donors is important to establish strong intermolecular interactions and in turn generate a more occlusive chemical species. Thus glycerol monobehenate has shown to be a "skin-like" fatty amphiphile that reduces water loss in vitro and has the potential to reduce water loss through the SC and thereby help in the treatment of xerotic skin conditions.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A topical oil-in-water emulsion composition comprising:
   a) a discontinuous oil phase;
   b) a continuous aqueous phase comprising water;
   c) a thickening agent;
   d) glyceryl monobehenate and/or ethylene glycol monobehenate; and
   e) at least one lamellar membrane structure comprising (i) a phospholipid, (ii) cetyl alcohol, (iii) isostearyl isostearate (ISIS), and (iv) behenic acid;
   wherein in use the composition has a water vapor transmission rate of less than about 70 g·m$^{-2}$·hr$^{-1}$ measured in vitro using the modWVTR test methodology, and
   wherein the composition does not contain behenyl alcohol.

2. The composition according to claim 1 which is free from an anionic surfactant and/or a ceramide.

3. The composition according to claim 1, wherein the phospholipid is hydrogenated phosphatidylcholine.

4. The composition according to claim 1, wherein the phospholipid is present in an amount from about 0.5% to about 5% by weight, based on the total weight of the composition.

5. The composition according to claim 1, wherein the cetyl alcohol is present in an amount from about 2% to about 15% by weight, based on the total weight of the composition.

6. The composition according to claim 1 wherein the cetyl alcohol and the phospholipid are present in a weight ratio from about 10:1 to about 1:1.

7. The composition according to claim 1, wherein the behenic acid is present in an amount from about 0.1% to about 5% by weight, based on the total weight of the composition.

8. The composition according to claim 1 wherein the phospholipid and behenic acid are present in a weight ratio from about 5:1 to about 1:5.

9. The composition according to claim 1, wherein the isostearyl isostearate is present in an amount from about 0.1% to about 5% by weight, based on the total weight of the composition.

10. The composition according to claim 1, wherein glyceryl monobehenate and/or ethylene glycol monobehenate is present in an amount from about 0.1 to about 10% by weight, based on the total weight of the composition.

11. The composition according to claim 10 wherein the amount of glyceryl monobehenate and/or ethylene glycol monobehenate is >3% w/w.

12. The composition according to claim 1 wherein the composition further comprises caprylic/capric triglyceride.

13. The composition according to claim 1 wherein the composition further comprises pentylene glycol, glycerin and gelling agents, and optionally other dermatologically acceptable excipients.

* * * * *